(12) United States Patent
Nihalani

(10) Patent No.: US 8,100,932 B2
(45) Date of Patent: Jan. 24, 2012

(54) METHOD AND APPARATUS FOR TREATING OBESITY AND CONTROLLING WEIGHT GAIN USING SELF-EXPANDING INTRAGASTRIC DEVICES

(75) Inventor: Raj Nihalani, Irvine, CA (US)

(73) Assignee: Onciomed, Inc., Irvine, CA (US)

( * ) Notice: Subject to any disclaimer, the term of this patent is extended or adjusted under 35 U.S.C. 154(b) by 492 days.

(21) Appl. No.: 12/415,823

(22) Filed: Mar. 31, 2009

(65) Prior Publication Data

US 2010/0249825 A1 Sep. 30, 2010

(51) Int. Cl.
*A61M 29/00* (2006.01)
(52) U.S. Cl. ........................................ 606/192
(58) Field of Classification Search .......... 606/191–200; 623/23.64–23.68; 604/99.01–99.04
See application file for complete search history.

(56) References Cited

U.S. PATENT DOCUMENTS

| | | | |
|---|---|---|---|
| 4,403,604 A * | 9/1983 | Wilkinson et al. ............. 600/37 |
| 4,592,339 A | 6/1986 | Kuzmak et al. |
| 4,696,288 A | 9/1987 | Kuzmak et al. |
| 4,739,758 A * | 4/1988 | Lai et al. ............................. 606/1 |
| 4,899,747 A * | 2/1990 | Garren et al. ................. 606/192 |
| 4,925,446 A * | 5/1990 | Garay et al. ............. 604/103.02 |
| 5,074,868 A | 12/1991 | Kuzmak |
| 5,129,915 A * | 7/1992 | Cantenys ....................... 606/192 |
| 5,308,326 A * | 5/1994 | Zimmon ..................... 604/103.1 |
| 5,449,368 A | 9/1995 | Kuzmak |
| 5,601,604 A | 2/1997 | Vincent |
| 5,910,149 A | 6/1999 | Kuzmak |
| 5,938,669 A | 8/1999 | Klaiber et al. |
| 6,511,490 B2 | 1/2003 | Robert |
| 6,547,801 B1 | 4/2003 | Dargent et al. |
| 6,558,400 B2 | 5/2003 | Deem et al. |
| 6,579,301 B1 * | 6/2003 | Bales et al. ................... 606/191 |
| 6,656,194 B1 | 12/2003 | Gannoe et al. |
| 6,676,674 B1 | 1/2004 | Dudai |
| 6,746,460 B2 | 6/2004 | Gannoe et al. |
| 6,755,869 B2 * | 6/2004 | Geitz ........................ 623/23.65 |
| 6,773,440 B2 | 8/2004 | Gannoe et al. |
| 6,981,978 B2 | 1/2006 | Gannoe |
| 6,994,715 B2 | 2/2006 | Gannoe et al. |
| 7,033,373 B2 | 4/2006 | de la Torre et al. |
| 7,033,384 B2 * | 4/2006 | Gannoe et al. ............... 623/1.11 |
| 7,083,629 B2 | 8/2006 | Weller et al. |
| 7,097,650 B2 | 8/2006 | Weller et al. |
| 7,175,638 B2 | 2/2007 | Gannoe et al. |
| 7,211,094 B2 | 5/2007 | Gannoe et al. |
| 7,214,233 B2 | 5/2007 | Gannoe et al. |
| 7,220,237 B2 | 5/2007 | Gannoe et al. |

(Continued)

FOREIGN PATENT DOCUMENTS

CN 101193610 6/2008
(Continued)

*Primary Examiner* — Gary Jackson
*Assistant Examiner* — Christopher Schubert
(74) *Attorney, Agent, or Firm* — Snell & Wilmer LLP

(57) ABSTRACT

The invention generally relates to a method and apparatus to treat obesity and controlling weight gain. In an exemplary embodiment, the invention relates to a covered cage device that is implanted within a human's stomach to occupy volume and cause a reduced desire for eating. The covered cage device is made from a wire-mesh, such a Nitinol, and can be adjustable and collapsible. In another embodiment, the covered cage device has edges that provide stimulation to the stomach to induce a feeling of fullness.

5 Claims, 32 Drawing Sheets

U.S. PATENT DOCUMENTS

| | | | |
|---|---|---|---|
| 7,229,428 B2 | 6/2007 | Gannoe et al. | |
| 7,288,099 B2 | 10/2007 | Deem et al. | |
| 7,288,101 B2 | 10/2007 | Deem et al. | |
| 7,306,614 B2 | 12/2007 | Weller et al. | |
| 7,320,696 B2 * | 1/2008 | Gazi et al. | 606/192 |
| 7,338,433 B2 | 3/2008 | Coe | |
| 7,367,937 B2 * | 5/2008 | Jambor et al. | 600/37 |
| 8,001,974 B2 * | 8/2011 | Makower et al. | 128/898 |
| 2003/0120288 A1 | 6/2003 | Benchetrit | |
| 2003/0158564 A1 | 8/2003 | Benchetrit | |
| 2003/0208212 A1 * | 11/2003 | Cigaina | 606/151 |
| 2004/0044354 A1 | 3/2004 | Gannoe et al. | |
| 2004/0088008 A1 | 5/2004 | Gannoe et al. | |
| 2004/0122452 A1 | 6/2004 | Deem et al. | |
| 2004/0122453 A1 * | 6/2004 | Deem et al. | 606/151 |
| 2005/0096638 A1 | 5/2005 | Starkebaum | |
| 2005/0119674 A1 * | 6/2005 | Gingras | 606/151 |
| 2005/0159769 A1 | 7/2005 | Alverdy | |
| 2005/0209702 A1 * | 9/2005 | Todd et al. | 623/20.33 |
| 2005/0251181 A1 * | 11/2005 | Bachmann | 606/157 |
| 2006/0282107 A1 * | 12/2006 | Hashiba et al. | 606/153 |
| 2007/0015955 A1 | 1/2007 | Tsonton | |
| 2007/0027356 A1 | 2/2007 | Ortiz | |
| 2007/0048334 A1 | 3/2007 | Aurora | |
| 2007/0048476 A1 * | 3/2007 | Park | 428/36.91 |
| 2007/0078476 A1 * | 4/2007 | Hull et al. | 606/191 |
| 2007/0083224 A1 * | 4/2007 | Hively | 606/192 |
| 2007/0100367 A1 * | 5/2007 | Quijano et al. | 606/192 |
| 2007/0112364 A1 | 5/2007 | Gerbi et al. | |
| 2007/0118168 A1 | 5/2007 | Lointier et al. | |
| 2007/0135829 A1 | 6/2007 | Paganon | |
| 2007/0156013 A1 | 7/2007 | Birk | |
| 2007/0156248 A1 * | 7/2007 | Marco et al. | 623/23.7 |
| 2007/0233161 A1 | 10/2007 | Weller et al. | |
| 2007/0250083 A1 * | 10/2007 | Deem et al. | 606/153 |
| 2007/0265645 A1 | 11/2007 | Birk et al. | |
| 2007/0276428 A1 * | 11/2007 | Haller et al. | 606/192 |
| 2008/0033574 A1 * | 2/2008 | Bessler et al. | 623/23.68 |
| 2008/0091076 A1 | 4/2008 | Roth et al. | |
| 2008/0091077 A1 | 4/2008 | Roth et al. | |
| 2008/0091078 A1 | 4/2008 | Roth et al. | |
| 2008/0091079 A1 | 4/2008 | Roth et al. | |
| 2008/0132925 A1 * | 6/2008 | Demarais | 606/157 |
| 2008/0208240 A1 | 8/2008 | Paz | |
| 2008/0208241 A1 * | 8/2008 | Weiner et al. | 606/192 |
| 2008/0208355 A1 * | 8/2008 | Stack et al. | 623/23.65 |
| 2008/0243166 A1 | 10/2008 | Paganon et al. | |
| 2009/0118756 A1 | 5/2009 | Valencon et al. | |
| 2009/0118757 A1 * | 5/2009 | Burnett et al. | 606/192 |
| 2009/0216262 A1 * | 8/2009 | Burnett et al. | 606/192 |
| 2010/0100115 A1 * | 4/2010 | Soetermans et al. | 606/192 |

FOREIGN PATENT DOCUMENTS

| | | |
|---|---|---|
| EP | 1205148 | 5/2002 |
| GR | 1002464 | 11/1996 |
| GR | 2007/0100015 | 9/2008 |
| WO | WO 01/41671 | 6/2001 |
| WO | WO 2004/014245 | 2/2004 |
| WO | WO 2008/122713 | 10/2008 |
| WO | WO 2009/059803 | 5/2009 |

* cited by examiner

METHOD AND APPARATUS FOR TREATING OBESITY AND CONTROLLING WEIGHT GAIN USING SELF-EXPANDING INTRAGASTRIC DEVICES

BACKGROUND

1. Field

The invention generally relates to a method and apparatus for treating obesity, excess weight gain, and controlling weight gain in mammals. More specifically, the invention relates to intragastric devices (e.g., one or more cages) placed within the stomach of a mammal to occupy volume and to cause a reduced desire for eating for treating obesity and controlling weight gain.

2. Related Art

Obesity is a major illness in the United States and other developed countries. More than half of Americans are overweight, while nearly one-third are categorized as obese. Obesity is the accumulation of excess fat on the body, and is defined as having a body mass index (BMI) of greater than 30. Many serious long-term health consequences are associated with obesity, such as, hypertension, diabetes, coronary artery disease, stroke, congestive heart failure, venous disease, multiple orthopedic problems and pulmonary insufficiency with markedly decreased life expectancy.

Medical management of obesity, such as dietary, psychotherapy, medication and behavioral modification techniques, have yielded extremely poor results in terms of treating obesity. In addition, several surgical procedures have been tried which have bypassed the absorptive surface of the small intestine or have been aimed at reducing the stomach size by either partition or bypass. These surgical procedures have been proven both hazardous to perform in morbidly obese patients and have been fraught with numerous life-threatening postoperative complications. Moreover, such operative procedures are often difficult to reverse.

Currently, in cases of morbid or severe obesity, patients may undergo several types of bariatric surgery, such as gastric bypass, either to tie off or staple portions of the large or small intestine or stomach, and/or to bypass portions of the same to reduce the amount of food desired by the patient, and the amount absorbed by the intestinal track. In addition, procedures such as laparoscopic banding, where a device is used to constrict a portion of the stomach, can also achieve these results.

In the case of gastric bypass surgery, laparoscopic banding and other highly invasive surgical procedures, several complications can arise that make these procedures clinically suboptimal. The surgical procedures require the patient to submit to an intervention under general anesthesia, and may require large incisions and lengthy recovery times. In addition, many of these surgical procedures are irreversible.

Therefore, a need exists for a minimally-invasive procedure and device that eliminates the above-mentioned drawbacks of conventional methods and devices that are currently being used to treat obesity and control weight gain.

SUMMARY

In one embodiment, the invention includes an intragastric space-occupying device configured to be positioned within a stomach for treating excessive weight or obesity in mammals, the device comprising: a first cage configured to be positioned along a lesser curvature of a stomach, the first cage having closed ends; a second cage configured to be connected to the first cage, the second cage having open ends and a hollow channel; and a third cage configured to be connected to the second cage, and further configured to be positioned along a greater curvature of the stomach, the third cage having closed ends.

In one embodiment, the invention includes an intragastric space-occupying device configured to be positioned within a stomach for treating excessive weight or obesity in mammals. The intragastric space-occupying device comprising a self-expanding wire mesh having an open top portion and an open bottom portion, a hollow center channel extending from the open top portion to the open bottom portion, and an elastomeric material positioned on the self-expanding wire mesh.

BRIEF DESCRIPTION OF THE DRAWINGS

These and other embodiments of the invention will be discussed with reference to the following exemplary and non-limiting illustrations, in which like elements are numbered similarly, and where.

DETAILED DESCRIPTION

Figure 1:
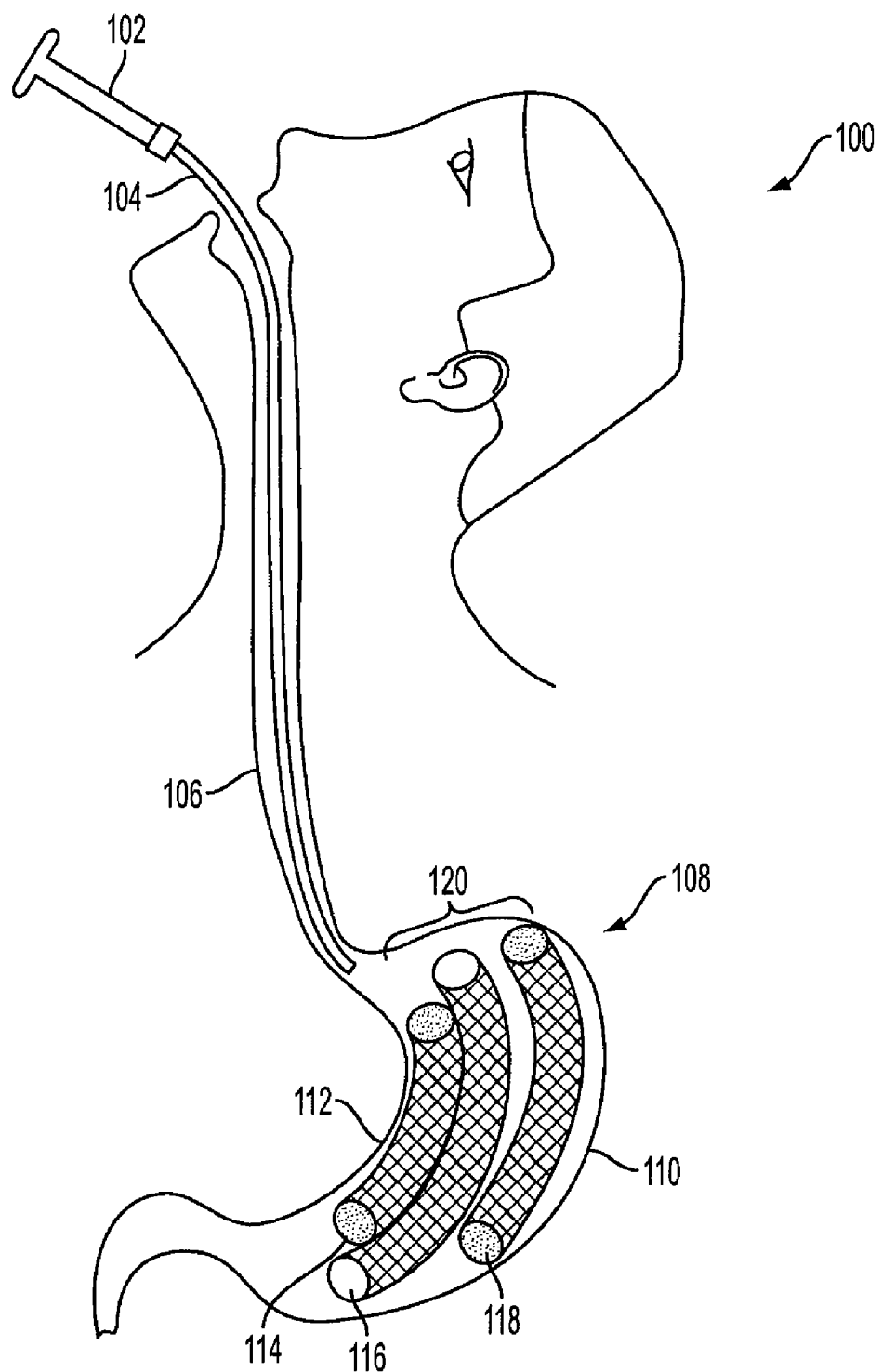
FIG. 1 is a partial view of a patient with an implanted intragastric triple-cage device according to an embodiment of the invention.

FIG. 1 is a partial view of a patient with an implanted intragastric triple-cage device 120. The triple-cage device 120 is placed within a stomach 108 of a mammal 100 (e.g., human) by a healthcare professional, such as a surgeon, a bariatric surgeon, or a gastrointestinal specialist trained in endoscopic surgery procedures. The triple-cage device 120 can be positioned within the stomach 108 using a routine endoscopic procedure. Furthermore, the triple-cage device 120 can be placed within the stomach 108 using newer techniques, methods and procedures for endoscopic surgery. Even though three cages are described herein, one, two, three, four, five, etc. cage(s) or device(s) may be positioned within the stomach 108 depending on the particular application and desired results.

The endoscopic delivery system includes an endoscopic device 102 and a sheath 104. The endoscopic device is used to insert a sheath 104 into an esophagus 106 of a human 100. Once the end of the sheath 104 reaches the stomach 108, a first cage 114, a second cage 116, and a third cage 118 are deployed into the stomach 108. The first cage 114 is configured to be positioned along a lesser curvature 112 of the stomach 108, while the third cage 118 is configured to be positioned along a greater curvature 110 of the stomach 108. The second cage 116 is configured to be positioned between the first cage 114 and the third cage 118.

Figure 2:
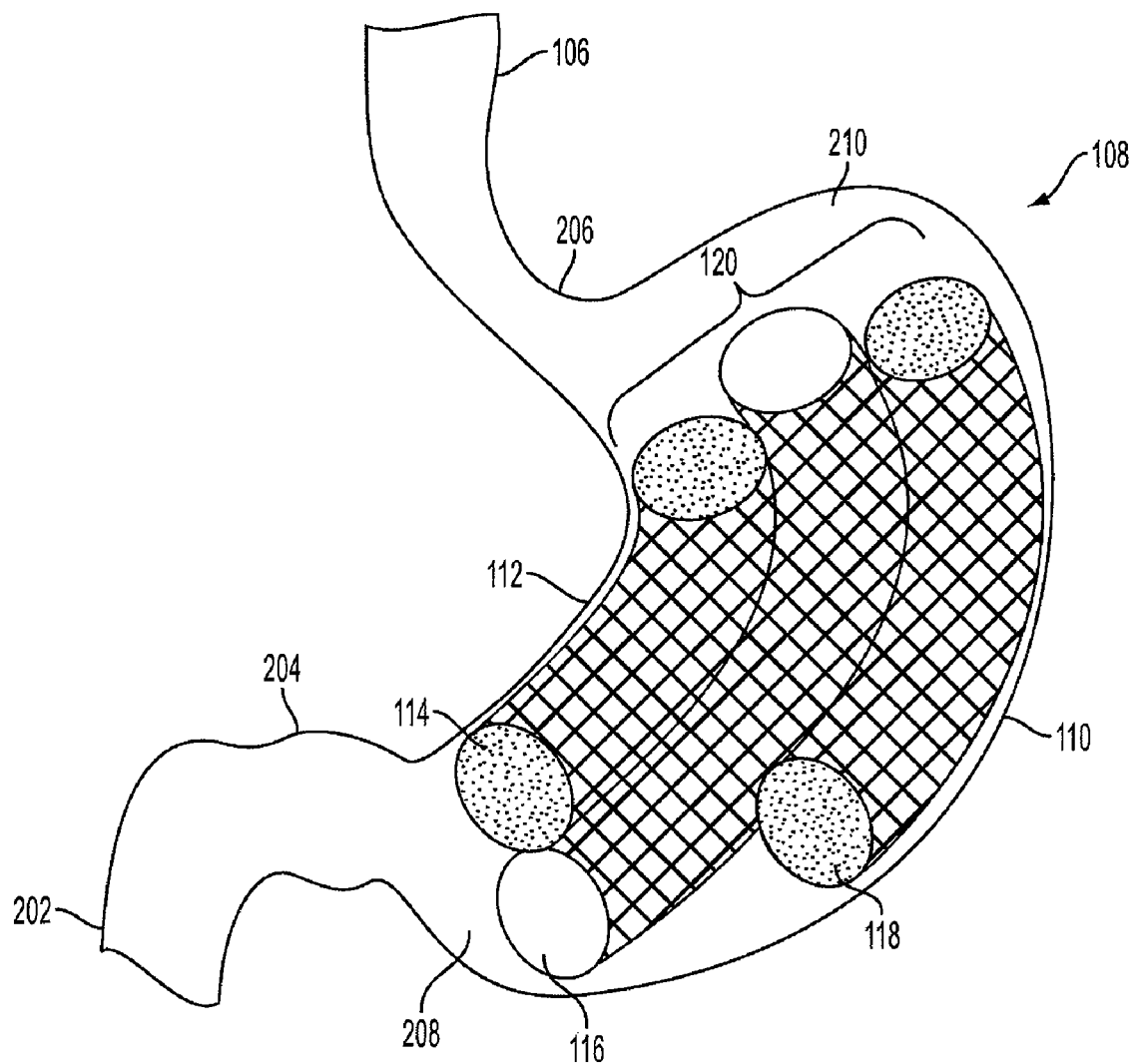
FIG. 2 is an exploded view of the triple-cage device implanted within the stomach of a human according to an embodiment of the invention.

FIG. 2 is an exploded view of the triple-cage device 120 implanted within the stomach 108 of a human 100. The stomach 108 has at least two curvatures, the lesser curvature 112 and the greater curvature 110. The cardia or proximal stomach 206 is located in the upper left portion of the stomach 108 and serves as the junction between the esophagus 106 and the body or inside of the stomach 108. The fundus 210 is located in the upper right portion of the stomach 108. The lower portion of the stomach 108 is known as the distal stomach 208, which includes a pyloric notch 204. The distal stomach 208 is where food is mixed with gastric juices. The pyloric notch 204 has a muscular pyloric sphincter that acts as a valve to control emptying of food and stomach contents into the proximal segment of the small intestine 202 (partially shown).

As shown in FIG. 2, the first cage 114 is positioned along the lesser curvature 112 of the stomach 108. The first cage 114 is substantially smaller in length than the second cage 116, and slightly smaller in length than the third cage 118. The second cage 116 is positioned between the first cage 114 and the third cage 118. The third cage 118 is positioned along the greater curvature 110. In an embodiment, the lengths of each of the cages can vary.

Each of the cages in the triple-cage device 120 has a curved cylindrical shape, such as a tube, similar to a banana, to conform to the natural shape of the stomach 108. In another embodiment, each cage can be rectangular or another multi-sided or smooth geometric shape instead of a cylindrical shape. Furthermore, the cages can be any type of geometric shape, such as, but not limited to, a sphere, square, cone, oval, torroid or doughnut. The cages can each have a different shape and size, and the design of the triple-cage device 120 is not limited to the illustration shown in FIG. 2.

The triple-cage device 120 can occupy approximately 50% to 95% of the volume of the stomach body. Preferably, the triple-cage device 120 can occupy approximately 70% to 80% of the volume of the stomach body. The triple-cage device 120 can be self-expanding to conform to size changes and movement of the stomach 108. In this way, the triple-cage device 120 can continually occupy a constant volume of the stomach 108 regardless of the shape or size of the stomach 108.

As shown in FIG. 2, the triple-cage device 120 does not completely occupy the fundus 210 or the cardia 206. The upper portion of the stomach 108 is not completely occupied so that food may accumulate in the upper portion of the stomach 108. Likewise, the distal stomach 208 is not completely occupied by the triple-cage device 120. Thus, the proximal segment of the small intestine 202 is not blocked and there can be proper channeling of food and stomach contents. In some prior art intragastric cage devices, the proximal segment of the small intestine 202 become covered by the device, thus restricting proper channeling of food out of the stomach 108. The blockage of the proximal segment of the small intestine 202 causes food accumulation within the stomach 108, and can lead to various gastro-intestinal ailments or symptoms.

In an embodiment, the second cage 116 has open ends and a hollow channel therebetween. Food can travel from the proximal stomach 206 to the distal stomach 208 via the hollow channel. The hollow channel of the second cage 116 allows a gaseous exchange between the lower and upper portions of the stomach 108. The second cage 116 increases gastric filling and slows gastric emptying as only a limited amount of food can travel through the hollow channel.

In an embodiment, the second cage 116 can extend through the duodenum of the intestine (not shown). The extension of the second cage 116 can form an endoluminal sleeve which empties contents of the stomach into the jejunum. The sleeve can be anchored at a top portion by the first cage 112 and the third cage 118, as the second cage 116 is connected to the first cage 112 and the third cage 118. In an embodiment, the sleeve can be held in place by staples to the intestine wall or held in place by the self-expanding force of the wire mesh.

In another embodiment, the sleeve can be covered by an elastomeric material, or alternatively, made entirely of an elastomeric material, such as silicone, thermoplastic polymers, or any combination thereof. The sleeve can be self-expanding or filled with air or liquid, such as, for example, saline or methylene blue. The methylene blue can be used to detect leaks in the sleeve. The sleeve can be used to fill the residual stomach called the gastric sleeve created after a partial removal of the stomach called sleeve gastrectomy procedure. The cage may also assist in resolving any leaks associated post operatively with a gastric sleeve procedure.

In an embodiment, the sleeve can be used to fill a residual portion of the stomach called the "gastric sleeve" that is created after a partial removal of the stomach during a sleeve gastrectomy procedure. The cage may also assist in resolving any leaks post-operative leaking which may be associated with a sleeve gastrectomy procedure.

Furthermore, the second cage 116 can help in reducing gastro-esophageal reflux ("gastric reflux") as the hollow channel allows food to channel from the upper portion of the stomach and prevents excessive accumulation of food near the cardia 206 and the fundus 210.

Figure 3:
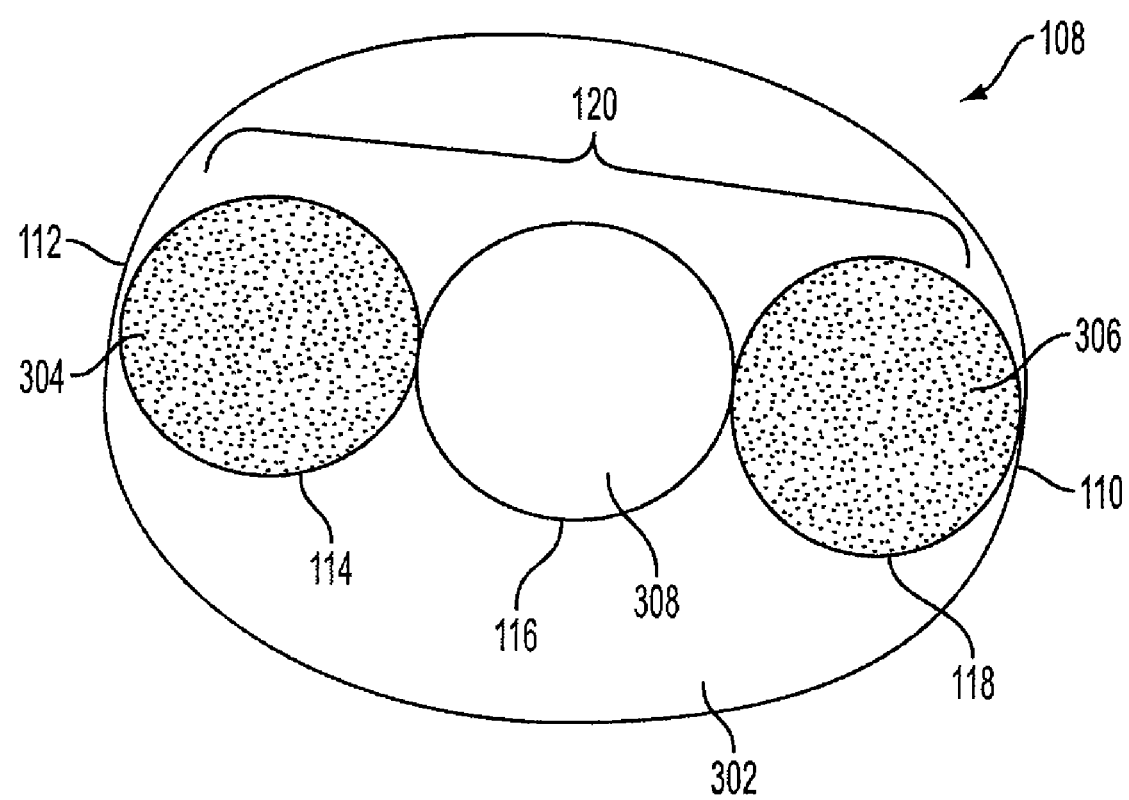
FIG. 3 is a cross-sectional top view of the stomach with the triple-cage device positioned within the stomach according to an embodiment of the invention.

FIG. 3 is a cross-sectional top view of the stomach 108 with the triple-cage device 120 positioned within the stomach 108. In an embodiment, the first cage 114, the second cage 116, and the third cage 118 are positioned in a substantially linear fashion, so that the second cage 116 is positioned between the first cage 114 and the third cage 118. As shown in FIG. 3, the triple-cage device 120 does not occupy the entire area of the stomach 108. As such, approximately 5% to 50% of open space 302 remains in the stomach 108 when the triple-cage device 120 is implanted. The open space 302 allows food to accumulate and slowly and properly channel toward the lower portion of the stomach 108 (not shown) as described above. In an embodiment, the first cage 114 may have a closed end 304, and the third cage 118 may have a closed end 306. Both ends of the first cage 114 and the third cage 118 may be closed and may be filled with air or other gas. The second cage 116 has an open top end 308 and an open bottom end (see also FIG. 2) which allow food to channel to the lower portion of the stomach 108, as well as allows a gaseous exchange between the lower and upper portions of the stomach 108.

In another embodiment, the first cage 114, the second cage 116, and the third cage 118 may not be positioned in a linear fashion, but rather can be positioned in a staggered manner so that the triple-cage device 120 is arranged in a different shape, for example, a triangular shape. Alternatively, the first cage 114 may not be positioned along the lesser curvature 112, and the third cage 118 may not be positioned along the greater curvature 110.

Figure 4:
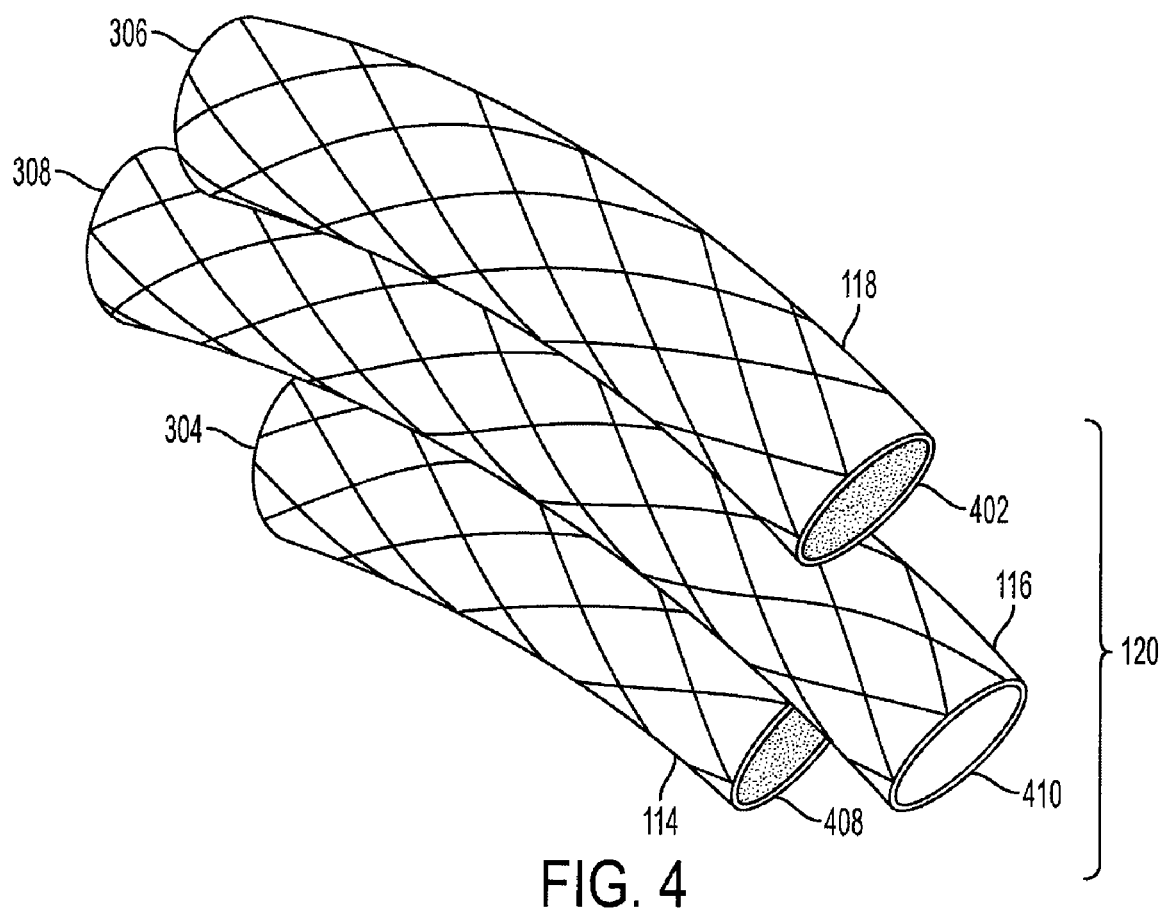
FIG. 4 is a perspective side view of the triple-cage device according to an embodiment of the invention.

FIG. 4 is a perspective side view of the triple-cage device 120. The first cage 114 has a closed top end 304 and a closed bottom end 408. The third cage 118 also has a closed top end 306 and a closed bottom end 402. The second cage 116 has an open top end 308 and an open bottom end 410. Alternatively, the first cage 114 and the third cage 118 can each have an open top end and an open bottom end which allows food to channel to the lower portion of the stomach 108, as well as allows a gaseous exchange between the lower and upper portions of the stomach 108.

Each cage can be a cylindrical air-filled cage, and can be coated or covered with an elastomeric material, such as ePTFE, Dacron®, or silicon. The cage cages are a wire mesh and are preferably made of nickel titanium (Nitinol) or stainless steel wire cage, Aluminum, Tungsten, Copper, Cobalt, Chromium, Gold, or other alloys which provide each cage with a self-expanding memory. The unique characteristic of Nitinol is that it has a thermally triggered shape memory. This allows each cage to be crimped per a desired length, width, and volume based on the cage sizes required per the patient's stomach dimensions. The crimped cages are then enclosed into a sheath for endoscopic delivery. The cages regain their desired shape when deployed into the stomach at body temperature, such as the temperature of the human body or the temperature of the stomach body. The term "stent" or "wire mesh" can also be used in place of the term "cage" throughout the disclosure.

In an embodiment, the semi-rigid or rigid Nitinol or thicker stainless steel wire frame is covered with ePTFE, silicone, Dacron® or any other elastomeric or thermo-elastomeric material. The desired shape of each cage is retained even under pressure from the stomach lining (not shown) since the cages are rigid wire cages made from Nitinol, stainless steel, or titanium that have a memory-retained shape. In a preferred embodiment, the self-expanding Nitinol cages are covered with a slightly dense, non-porous or semi-porous ePTFE.

The Nitinol or stainless steel wire used to create the cages allows the triple-cage device is designed to remain within a patient for a longer duration than conventional intragastric cages made of silicone. In contrast, a conventional intragastric cage made of silicone and filled with saline may be subject to degradation and leakage, and may be removed within a six months of being implanted into the patient, and in many cases, must be removed within 6 months or less. The triple-cage device 120 can remain implanted in the human for an extended period of time so that the human can achieve a desired weight loss.

In another embodiment, the first cage 114 and the second cage 118 are made entirely of silicone, other elastomers, thermoplastic polymers, or any combination thereof, and may be filled with air or liquid (e.g., saline) and methylene blue. The methylene blue is used to detect leaks in the cages.

Figure 5:
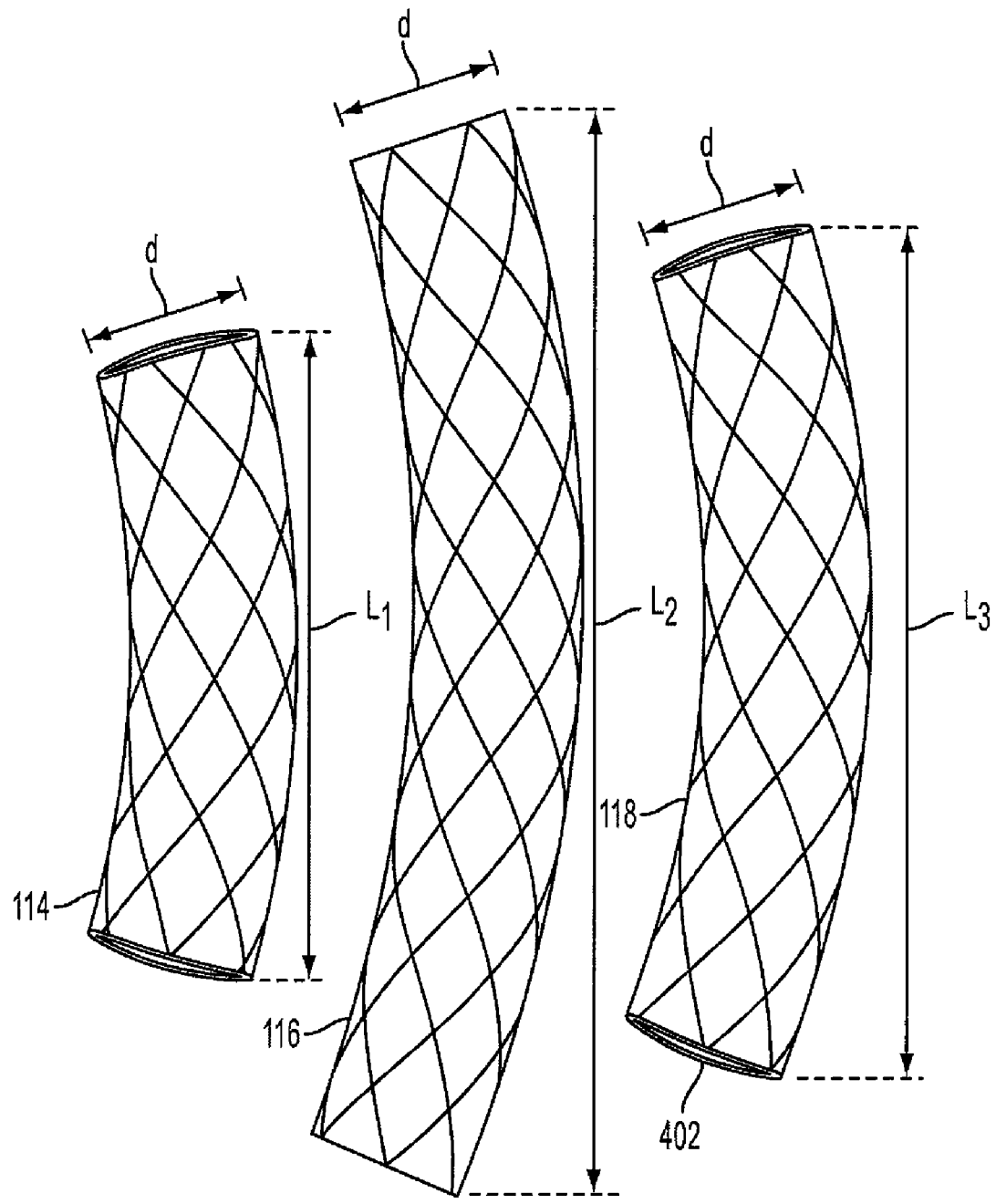
FIG. 5 is a view of three unconnected cages that make up the triple-cage device according to an embodiment of the invention.

FIG. 5 is a view of three unconnected cages that make up the triple-cage device 120. Each of the cages has a diameter d ranging from approximately 2 centimeters to 6 centimeters. In a preferred embodiment, the diameter d is approximately 4 centimeters. The first cage 114 can have a length $L_1$ of approximately 5 centimeters to 19 centimeters, and in a preferred embodiment, has a length $L_1$ of approximately 15 centimeters. The second cage 116 can have a length $L_2$ of approximately 6 centimeters to 30 centimeters, and in a preferred embodiment, has a length $L_2$ of approximately 20-25 centimeters. The third cage 118 can have a length $L_3$ of approximately 6 centimeters to 30 centimeters, and in a preferred embodiment, has a length $L_3$ of approximately 15-20 centimeters.

In a preferred embodiment, the first cage 114 has a volume of approximately 150-300 cubic centimeters, the second cage 116 has a volume of approximately 200-400 cubic centimeters, and the third cage 118 has a volume of approximately 200-500 cubic centimeters.

In another embodiment, all of the cages, or alternatively, only two of the cages, can have the same length. Furthermore, each of the cages can have a different diameter. The diameters and lengths of each cage can be adjusted by a healthcare professional based on the specific characteristics of the patient's stomach.

Figure 6:
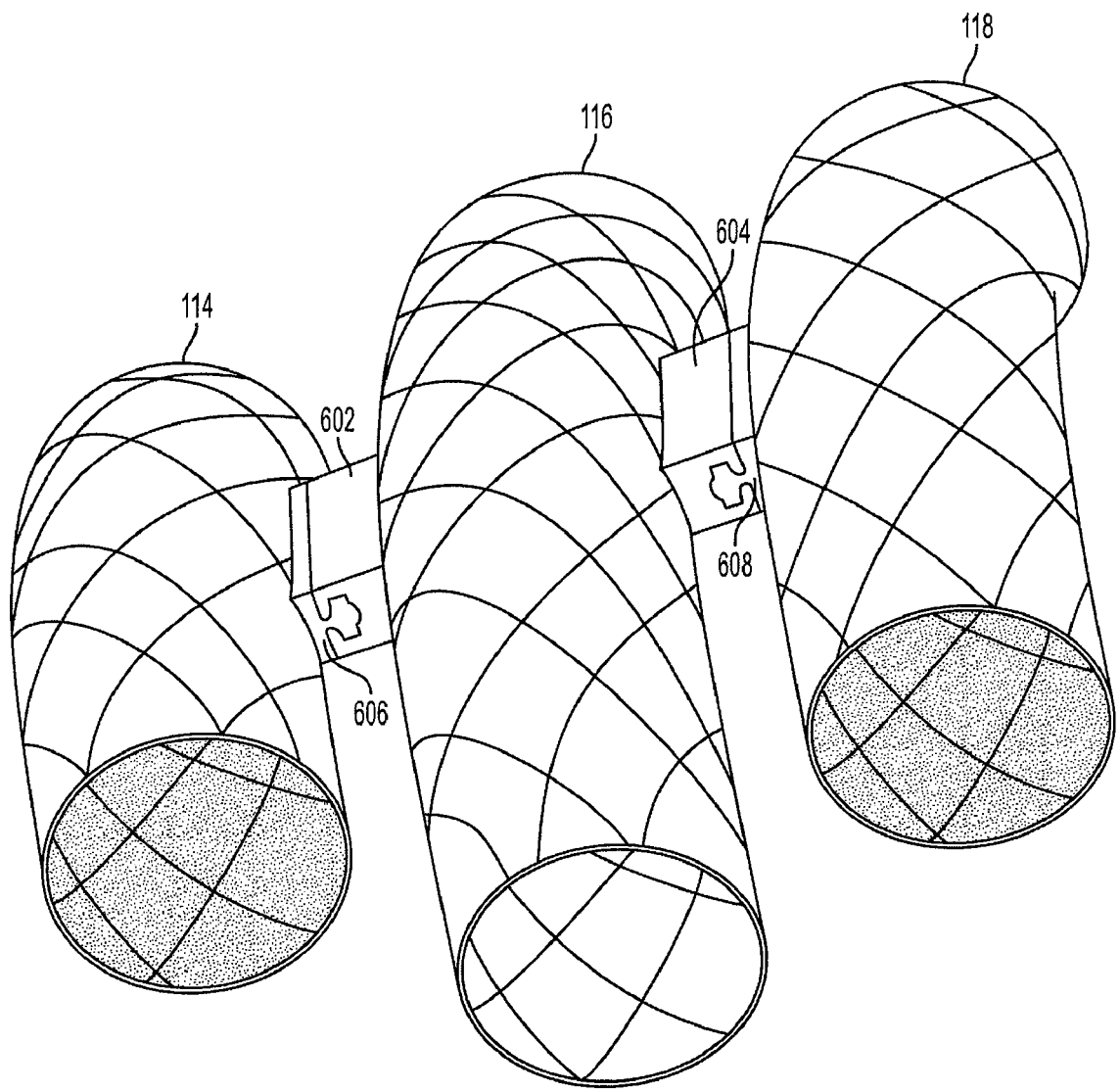
FIG. 6 is a view of the triple-cage device with connecting members according to an embodiment of the invention.

FIG. 6 is a view of the triple-cage device with connecting members. In an embodiment, the second cage 116 includes a first track 602 and a second track 604. The first track 602 is designed to slide into a rail 606 on the first cage 114, and the second track 604 is designed to slide into a rail 608 on the third cage 118. The tracks and rails are preferably made from a hardened surgical-grade stainless steel material. Alternatively, the tracks and rails can be made from a medical-grade, rigid polymer or thermoplastic material.

In another embodiment, the second cage 116 has only one track, either the first track 602 or the second track 604, and the second cage 116 is connected to only one of the other cages. In yet another embodiment, the triple-cage device 120 does not have any tracks, and each of the cages is held into position by the force of the inner wall pressure of the stomach.

In an embodiment, the connecting members can extend along the entire length of the cages. This design prevents the first cage 114 and the third cage 118 from shifting or bending in an opposite direction from the second cage 116. Furthermore, each side of the second cage 116 can have multiple tracks spaced apart along its exterior in a linear fashion instead of a single track on each side of the second cage 116.

In another embodiment, the track 602 can be positioned off-center toward the open top end 308 of the second cage 116. The track 602 can be positioned off-center in an opposite direction toward the open bottom end 410 of the second cage 116. This design allows a staggered placement of the first cage 114 relative to the third cage 118. The triple-cage device 120 also provides the center cage support to avoid kinking of the central tract. The cage can be viewed via an X-ray, ultrasound or CT to observe the placement of the cages.

Figure 7:
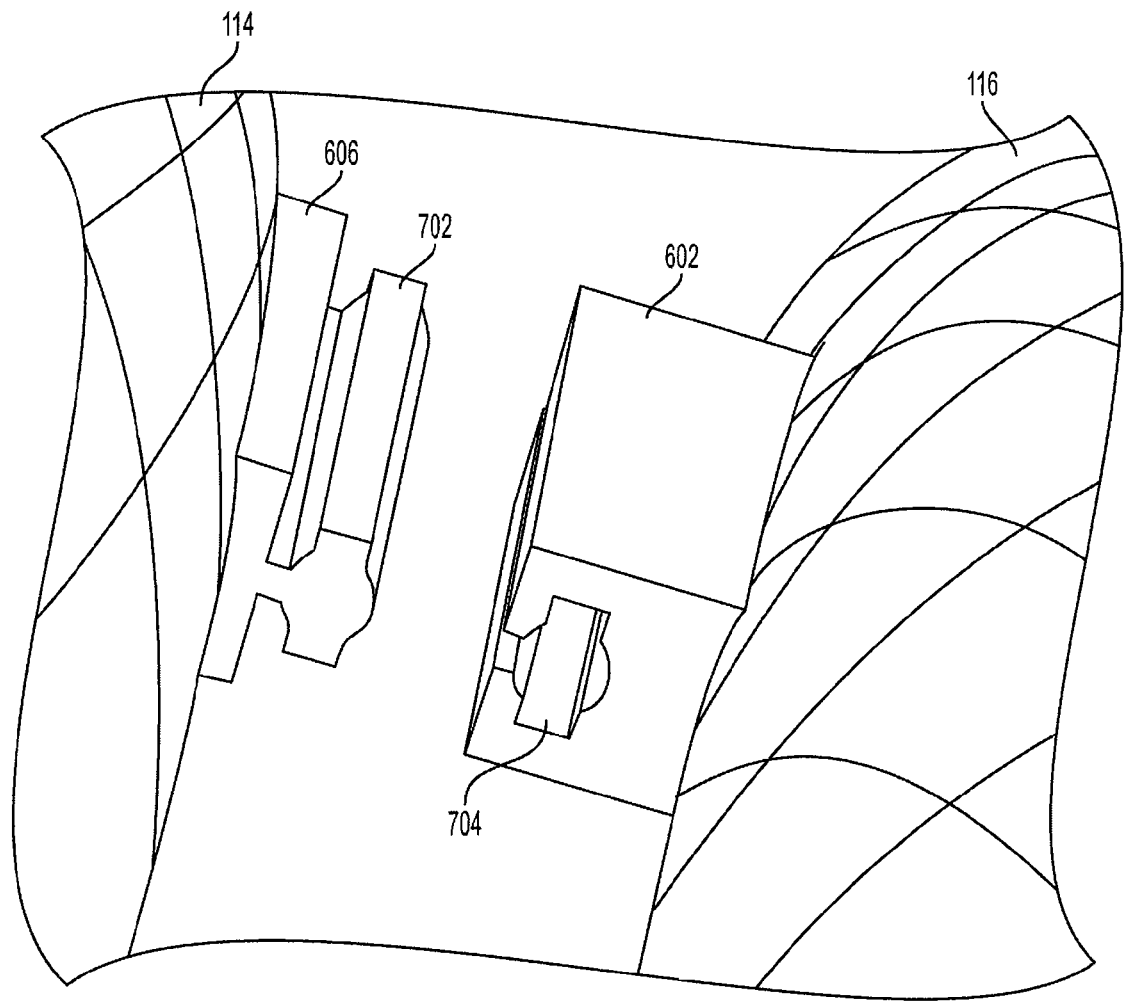
FIG. 7 is a view of an unconnected rail and track for the triple-cage device according to an embodiment of the invention.

FIG. 7 is a view of an unconnected rail and track for the triple-cage device. In one embodiment, the rail 606 is designed to slide into the track 602. The shape of the rail head 702 allows it to fit inside the receiving cavity 704 on the track 602, interlocking the rail 606 and the track 602. The rail head 702 can have any type of design which permits it to be interlocked with a corresponding design of the receiving cavity 704.

The connecting members are not limited to the rail design shown in FIGS. 6 and 7, and the second cage 116 can be equipped with clips, interlocking members, fasteners, or any other type of connecting means so that the second cage 116 can be secured to the first cage 114 and the third cage 118. In another embodiment, the first cage 114 and the third cage 118 can be directly connected to one another with any type of connecting means.

In another embodiment, the three cages are connected by a string, rope, or wrap that encircles the triple-cage device and holds the cages together. The string, rope or wrap can be made from an elastomeric material, such as silicone, or alternatively, can be made from Nitinol, a steel wire mesh, or a bioabsorbable polymer or material or a combination of polymers.

Figure 8:
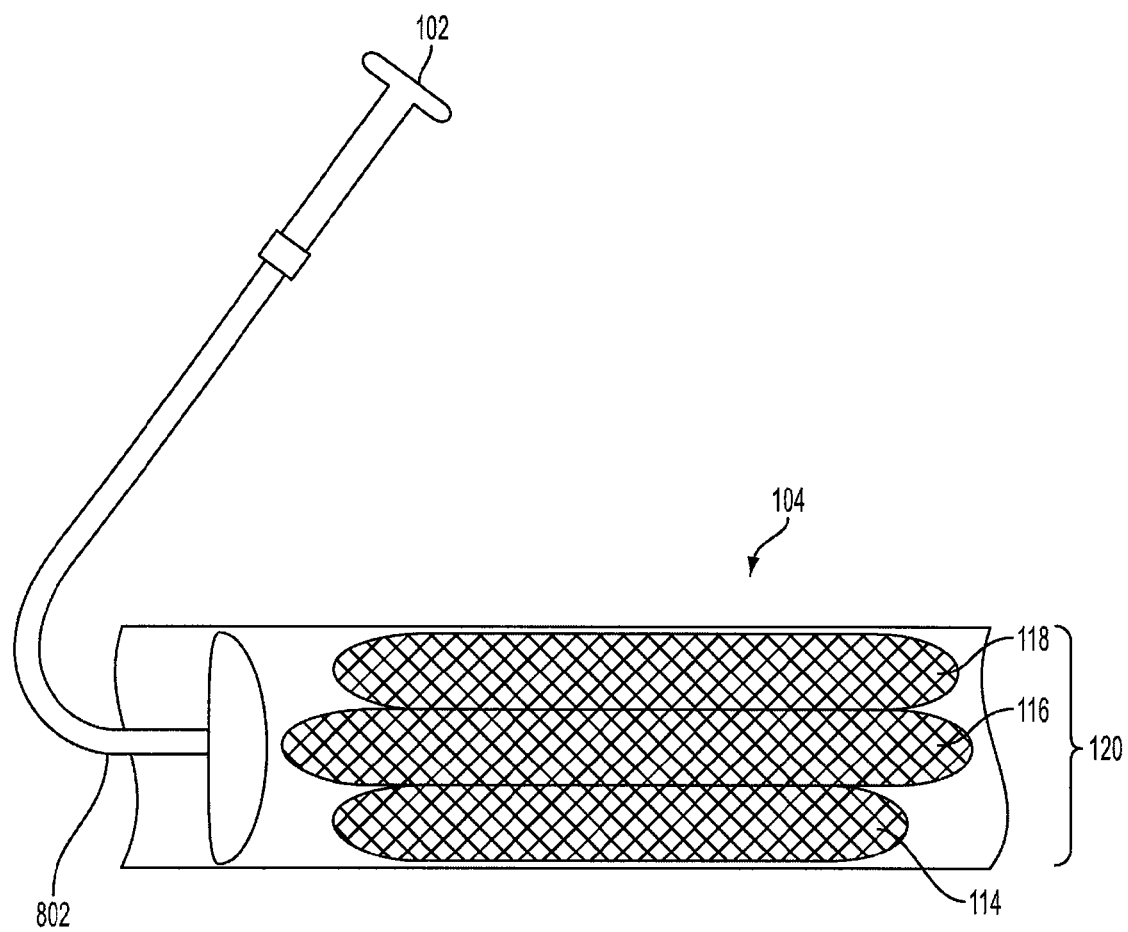
FIG. 8 is a view of a crimped triple-cage device within a sheath for delivery into the stomach according to an embodiment of the invention.

FIG. 8 is a view of a crimped triple-cage device 120 within a sheath 104 for delivery into the stomach. The triple-cage device 120 is crimped or collapsed so that is fits within the diameter of the sheath 104. A push-pull rod 802 operated by the healthcare professional via the endoscopic device 102 is used to deliver the triple-cage device 120 into the stomach.

In an embodiment, the first cage 114, the second cage 116, and the third cage 118 are pre-connected so that the triple-cage device is pre-assembled and the tracks are connected to their respective rails prior to being implanted into the human.

Upon delivery into the stomach, each cage expands and the triple-cage device 120 is positioned between the inner curvature and the outer curvature of the stomach. In another embodiment, the healthcare professional can adjust the position of the triple-cage device 120 after the cages have expanded using the endoscopic device 102. In another embodiment, each of the crimped cages can be color coded to assist the healthcare professional with orienting the triple-cage device 120 into the sheath 104.

The endoscopic device 102 can also be fitted with a cage retrieval device (not shown) that is used to retrieve the cages from the human's stomach. In an embodiment, the retrieval device is a clamp or a plurality of claws configured to exert a clamping force onto a section of one or more of the cages. The cages can then be retracted into the sheath 104, or any type of endoscopic sheath, one by one by the healthcare professional using the endoscopic device 102.

Figure 9:
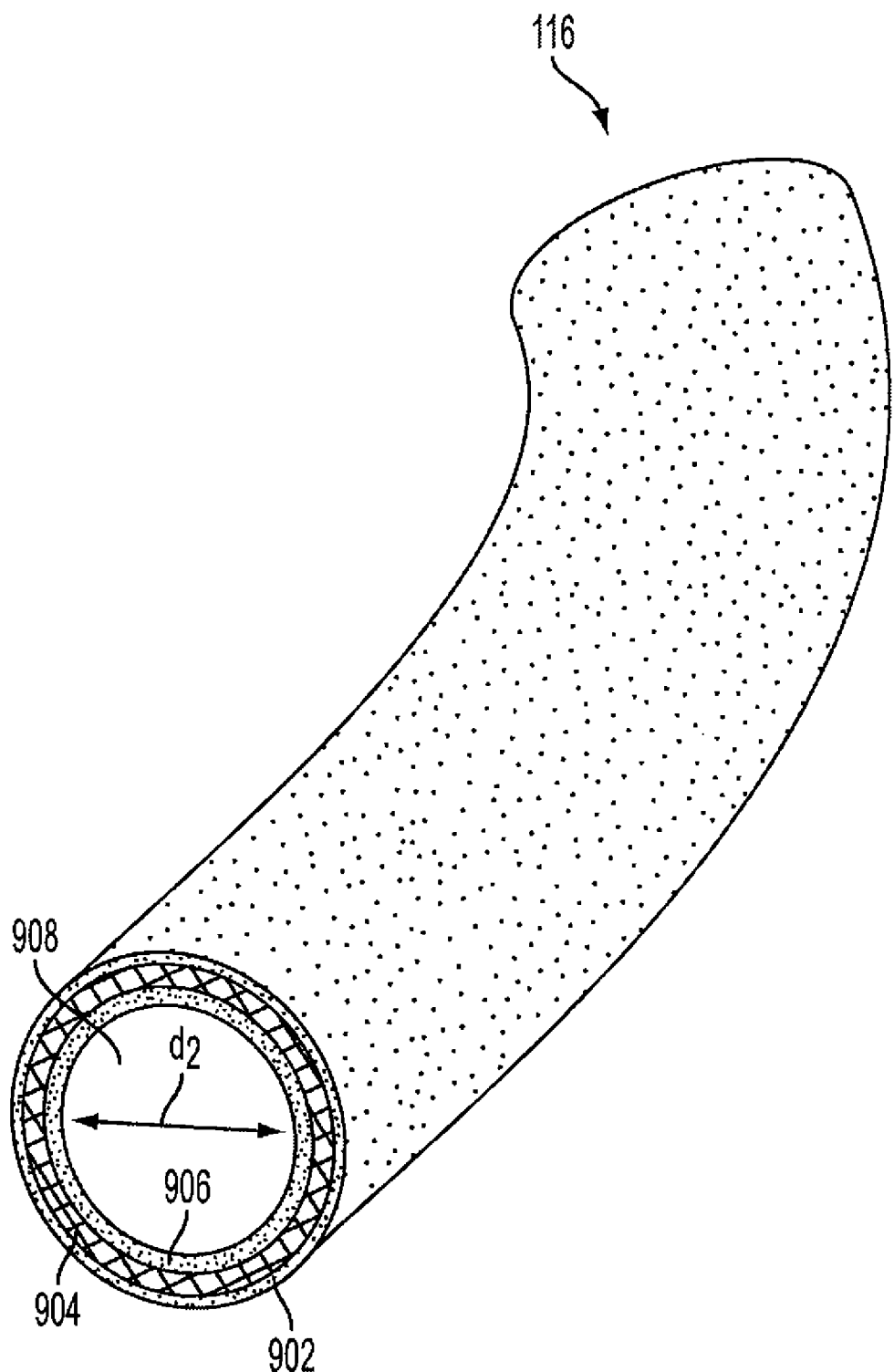
FIG. 9 is a view of the second cage with the hollow channel according to an embodiment of the invention.

FIG. 9 is a view of the second cage 116 with the hollow channel 908. The second cage 116 has the hollow channel 908 to channel food from the upper portion of the stomach to the lower portion of the stomach as described above. In an embodiment, the wire cage 904 of the second cage 116 is covered with an outer layer 902 made of ePTFE, Dacron®, or silicon or any other elastomeric or thermo-elastomeric material. The wire cage 904 is also covered with an inner layer 906 made of an elastomeric material. The outer layer 902 and the inner layer 906 can be the same material, or alternatively, can be different materials. The inner layer 906 prevents food and other stomach contents from being stuck onto the wire cage 904 when passing through the hollow channel 908. In an alternative embodiment, the second cage 116 only contains the inner layer 906 and does not contain the outer layer 902.

The diameter $d_2$ of the hollow channel 908 is preferably approximately 3 centimeters, and can vary based on the thicknesses of the outer layer 902 and the inner layer 906. The thickness of the outer layer 902 can range from approximately $5/1000$ to $60/1000$ inches.

Figure 10:
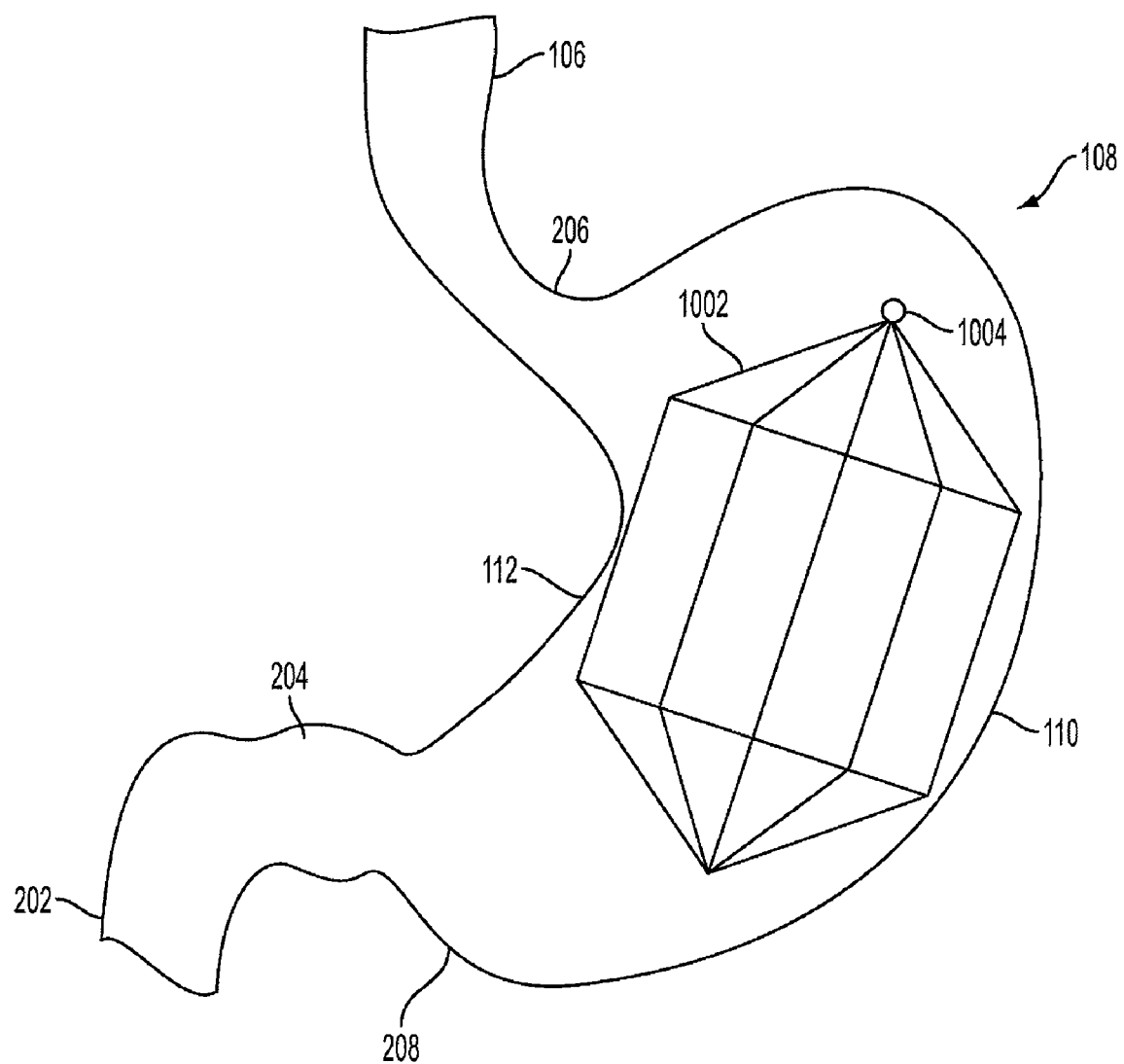
FIG. 10 is a view of a single lantern-shaped cage device positioned within the stomach according to an embodiment of the invention.

FIG. 10 is a view of a single lantern-shaped cage device 1002 positioned within the stomach 108. The lantern 1002 is air-filled, as opposed to being filled with a fluid or a liquid. In one embodiment, the lantern 1002 has an octagonal shape. However, the lantern 1002 can be formed in the shape of a circle, cylinder, triangle, tetragon, pentagon, hexagon, septagon, nonagon, decagon, or any other geometric shape. The lantern 1002 has a tip 1004 that allows the lantern 1002 to be collapsed and retrieved through an endoscopic procedure.

The lantern 1002 is preferably made of Nitinol, a stainless steel or a stainless steel alloy, copper or tungsten wire cage which provides the lantern 1002 with a self-expanding memory. This allows the lantern 1002 to be crimped per a desired length, width, and volume based on the human's stomach dimensions, and then placed into a sheath for endoscopic delivery. The lantern 1002 regains its desired shape when deployed into the stomach 108 at a certain temperature, such as the temperature of the human body or the temperature of the body of the stomach 108.

In one embodiment, the self-expanding Nitinol cage or stainless steel wire cage lantern 1002 is covered with an ePTFE, Dacron®, or silicon coating or covering. In a preferred embodiment, the lantern 1002 is covered with a slightly dense, non-porous or semi-porous ePTFE.

Figure 11:
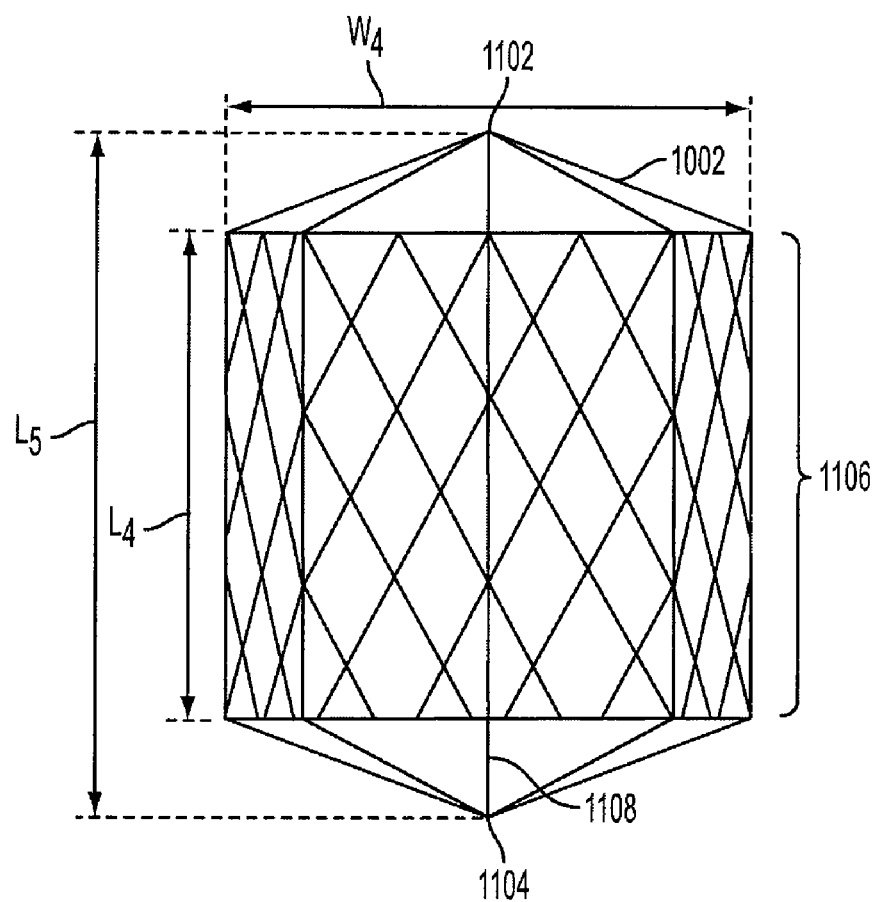
FIG. 11 is a side view of a single lantern-shaped cage device according to an embodiment of the invention.

FIG. 11 is a side view of a single lantern-shaped cage device 1002. The lantern 1002 has a top portion 1102, a bottom portion 1104, and edges 1106. In the shown embodiment, the lantern 1002 has an octagonal shape, thus the top portion 1102 has eight edges, and the bottom portion 1104 has eight edges. The edges 1106 innervate the gastric tissue along the inside of the stomach 108, thus creating a sensation of satiety to the human. In an alternative embodiment, the lantern 1002 can have multiple smooth, rounded edges.

In a preferred embodiment, the width $W_4$ of the lantern 1002 is approximately 5-15 cm, the length $L_4$ of the sides between the top portion 1102 and the bottom portion 1104 is approximately 7-20 centimeters, and the length $L_5$ of the entire lantern 1002 is approximately 5-25 centimeters.

In an embodiment, the lantern 1002 can occupy between approximately 0.25 L and 1.5 L of volume within the stomach body. In a preferred embodiment, the lantern 1002 is designed to occupy approximately 1.26 L of volume within the stomach body.

The width and length of the lantern 1002 can be modified based on the dimensions of the human's stomach. Thus, each individual may have a lantern 1002 with specific dimensions based on their stomach size, and the space required to be occupied in their stomach in order to achieve a desired weight loss. In another embodiment, the lantern 1002 is manufactured so that one size fits all adult humans, while another smaller lantern is manufactured so that one size fits all pediatric humans.

In another embodiment, the cage can be tapered, so that one end has a larger diameter than the other. The cage can also have a double-tapered design, or just tapered ends. The tapered-end design is similar to the lantern design described above. In another embodiment, the cage has an hour-glass shape.

In an embodiment, all of the single-cage designs described above have are made from a self-expanding Nitinol cage or stainless steel wire cage that is covered with an ePTFE, Dacron®, or silicon coating or covering. The covering forms an air-tight, non-permeable, leak-proof seal that prevents air, liquid, food, and other matter from entering the diamond-shaped cage device. In another embodiment, a single wire, instead of a wire mesh or cage, can be used to construct the cage device.

Figure 12:
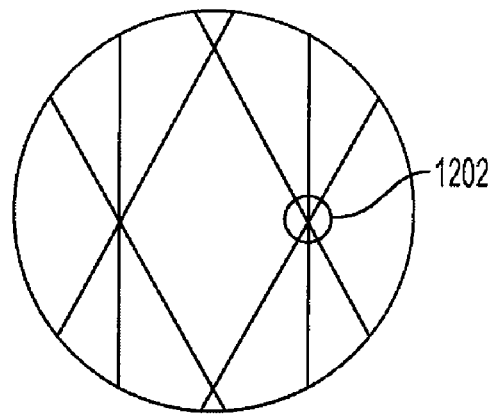
FIG. 12 is a view of the wire knitting of a lantern-shaped cage device according to an embodiment of the invention.

FIG. 12 is a view of the wire knitting of the lantern-shaped cage device 1002. The knitting 1202 illustrates the manner in which the Nitinol cage or stainless steel wire cage is constructed. The knitting 1202 can be done by hand, or alternatively, manufactured by a machine. The knitting 1202 used to connect the lantern wires can be achieved using any type of knot or tie, and is not limited by the embodiment shown in FIGS. 11 and 12. The lantern 1002 has a central spine 1108 that helps reinforce the shape. The central spine 1108 is also used in delivery and retrieval of the lantern.

In an embodiment, the knitting 1202 connects the wire mesh in a collapsible fashion. A string, cord, or spring (not shown) is attached at the top end 1102 and/or the bottom end 1104. Upon pressure to the string, cord, or spring, from an endoscopic retrieval device, the wire mesh collapses so that the lantern-shaped cage device 1002 can be pulled into a sheath.

In an embodiment, the cage device 1102 is in a collapsed or crimped form prior to being delivered into the patient's stomach. Once the collapsed cage device is released from the sheath into the stomach, it self-expands into a lantern shape. The self-expansion of the cage device occurs because of the Nitinol or wire mesh which has a shape-retaining memory. The present invention does not require the use of air, silicone, or any other substance to be pumped or inserted into the cage device in order to expand the device.

Figure 13:
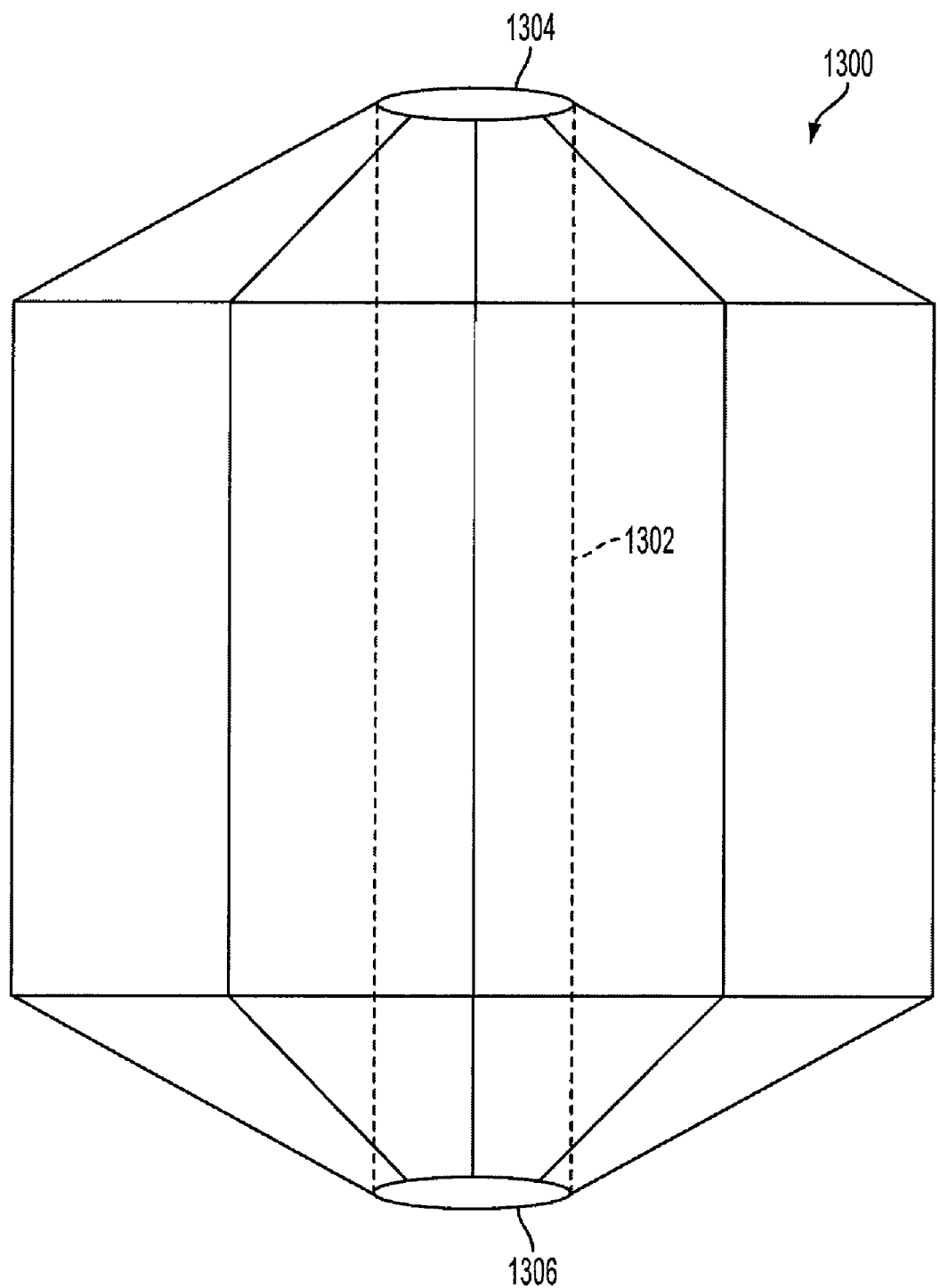
FIG. 13 is a view of a lantern-shaped cage device with a hollow center channel according to an embodiment of the invention.

FIG. 13 is a view of a lantern-shaped cage device 1300 with a hollow center channel 1302. In this embodiment, the lantern 1002 contains a hollow center channel 1302 with a top opening 1304 and a bottom opening 1306. The top opening 1304 allows some food to be channeled from the cardia and the fundus areas of the stomach down to the distal stomach. The hollow center channel 1302 operates in a similar manner and serves the same or a similar purpose as the hollow channel of the second cage 216 as described above in FIG. 2.

Figure 14:
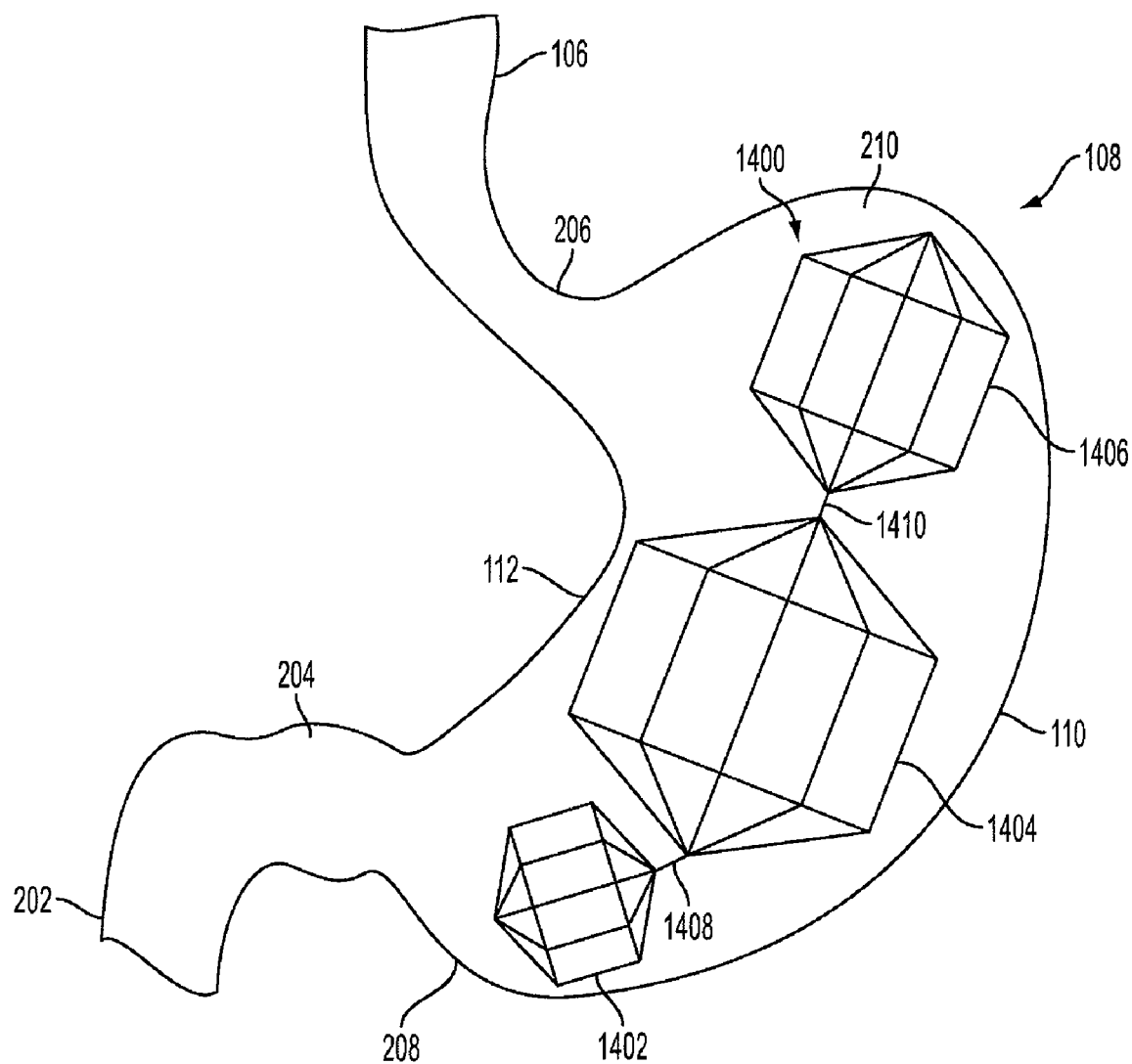
FIG. 14 is a view of a triple-lantern device implanted within the stomach according to an embodiment of the invention.

FIG. 14 is a view of a triple-lantern device 1400 implanted within the stomach 108. The triple-lantern device 1400 includes a first lantern 1402 that is positioned near the distal stomach 208. The first lantern 1402 is connected to a second lantern 1404 via a connector 1408. The second lantern 1404 is larger in volume than the first lantern 1402, and is connected to a third lantern 1406 via a connector 1410. The third lantern 1406 is larger in volume than the first lantern 1402, but smaller in volume than the second lantern 1404. The third lantern 1406 is positioned in the upper stomach near the fundus 210.

Each of the lanterns has a similar design and is made of similar materials as the lantern-shaped cage 1002 described in FIG. 10. Furthermore, the lanterns are not limited to the octagonal shape shown in FIG. 14, and can be any geometric shape as described above for the lantern-shaped cage 1002.

In an embodiment, the first lantern 1402 can occupy up to 0.3 L (300 cubic centimeters) of volume within the stomach body. In a preferred embodiment, the first lantern 1402 is designed to occupy approximately 150 cubic centimeters of volume within the stomach body. The first lantern 1402 can have a length of between approximately 3 centimeters and 5 centimeters, and in a preferred embodiment, can have a length of approximately 4 centimeters. The diameter of the first lantern 1402 can be between approximately 3 centimeters to 8 centimeters. In a preferred embodiment, the diameter of the first lantern 1402 is approximately 4 centimeters.

In an embodiment, the second lantern 1404 can occupy between approximately 0.1 L (500 cubic centimeters) and 0.8 L (800 cubic centimeters) of volume within the stomach body. In a preferred embodiment, the second lantern 1404 is designed to occupy approximately 700 cubic centimeters of volume within the stomach body. The second lantern 1404 can have a length of between approximately 5 centimeters and 8 centimeters, and in a preferred embodiment, can have a length of approximately 6 centimeters. The diameter of the second lantern 1404 can be between approximately 3 centimeters and 10 centimeters. In a preferred embodiment, the diameter of the second lantern 1404 is approximately 6 centimeters.

In an embodiment, the third lantern 1406 can occupy between approximately 0.1 L (300 cubic centimeters) and 0.5 L (500 cubic centimeters) of volume within the stomach body. In a preferred embodiment, the third lantern 1406 is designed to occupy approximately up to 250 cubic centimeters of volume within the stomach body. In a preferred embodiment, the entire triple-lantern device 1400 is designed to occupy approximately up to 1.2 L of volume within the stomach body. One, two, three, or more lantern devices 1400 can be used depending on the human's desired weight loss goals.

Figure 15:
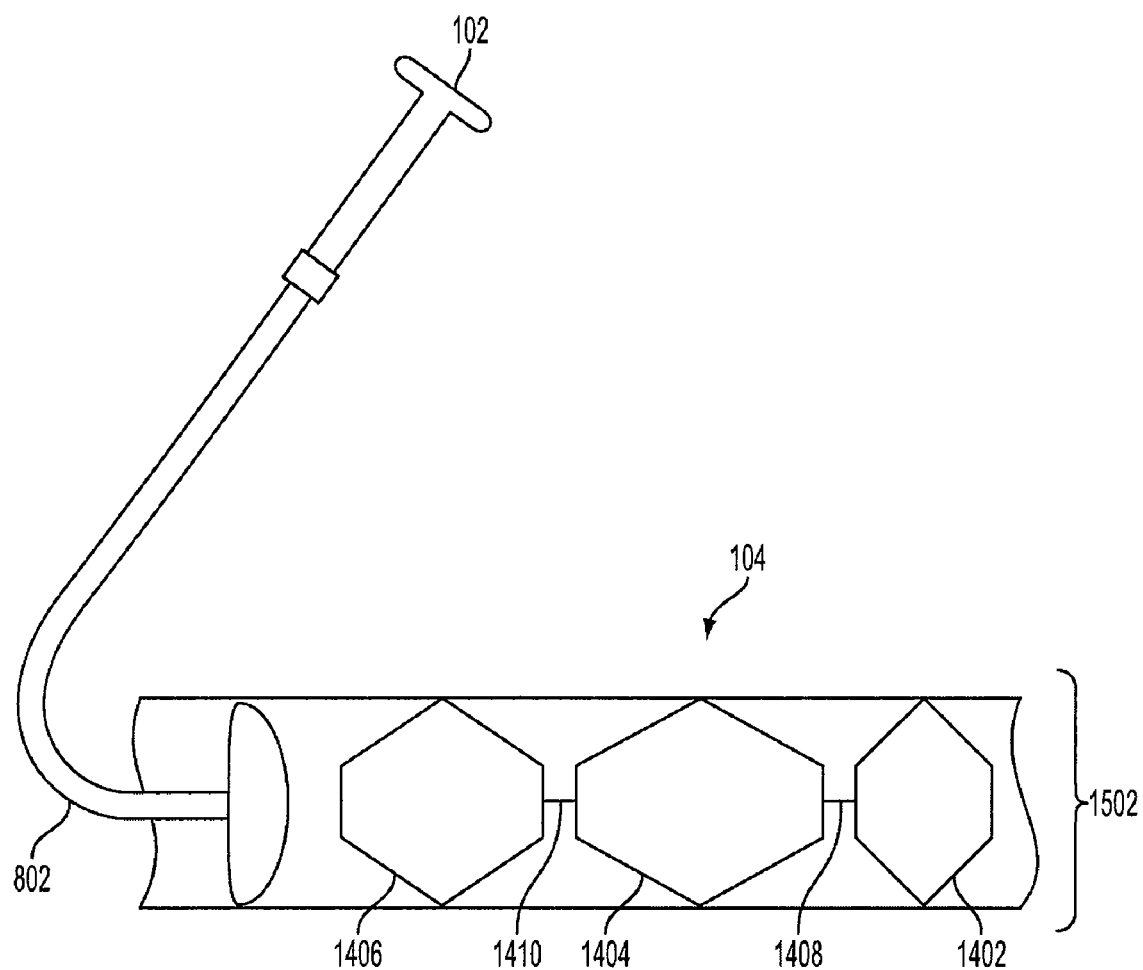
FIG. 15 is a view of a crimped triple-lantern device within a sheath prior to delivery into the stomach according to an embodiment of the invention.

FIG. 15 is a view of a crimped triple-lantern device 1502 within a sheath 104 prior to delivery into the stomach. The triple-lantern device 1502 is crimped or compressed so that is fits within the diameter of the sheath 104. A push-pull rod 802 operated by the healthcare professional via the endoscopic device 102 is used to deliver the triple-lantern device 1502 into the stomach 108. Each of the cages can have a central spine for providing support as the cages travel to the stomach 108.

In an embodiment, the first lantern 1402, the second lantern 1404, and the third lantern 1406 are pre-connected via the connectors 1408 and 1410 as described above. Upon delivery into the stomach 108, each lantern expands and the triple-lantern device 1502 is positioned within the inner curvature and the outer curvature of the stomach 108. In another embodiment, the healthcare professional can adjust the position of the triple-lantern device 1502 after the lanterns have expanded using the endoscopic device 102. In an embodiment, each of the crimped lanterns can be color-coded to assist the healthcare professional with orienting the triple-lantern device 1502 into the sheath 104.

The endoscopic device 102 can also be fitted with a lantern retrieval device (not shown) that is used to retrieve the lanterns from the human's stomach as described above. The lanterns can then be retracted into the sheath 104 one by one by the healthcare professional using the endoscopic device 102. The endoscopic device 102 can be adjusted if the human has obstruction or discomfort. For example, a single cage can be removed and the other two can be remain in the stomach.

In another embodiment, the first cage 114 and the third cage 118 can be made of silicone instead of wire cages. The silicone cages are filled with air that is injected through a port. The port can be locked in place once the desired amount of air pressure in the cage has been achieved. Alternatively, the silicone cages can be filled with saline, silicone, or nutrient supplements or bulking agents in a similar manner as above.

The benefit of having air, saline or nutrient or food supplement or bulking agent filled silicone cages is that they can diffuse nutrients and cause a feeling of fullness, and thus the cages will not settle at the lower portion of the stomach, and will remain in position at the upper and central location within the stomach. Having objects settle at the bottom of the stomach may cause discomfort to the patient. The silicone cages are lightweight and do not cause a feeling of heaviness in the stomach. Furthermore, by remaining in the central location within the stomach, the cages cause satiety and provide a feeling of fullness.

Figure 16:
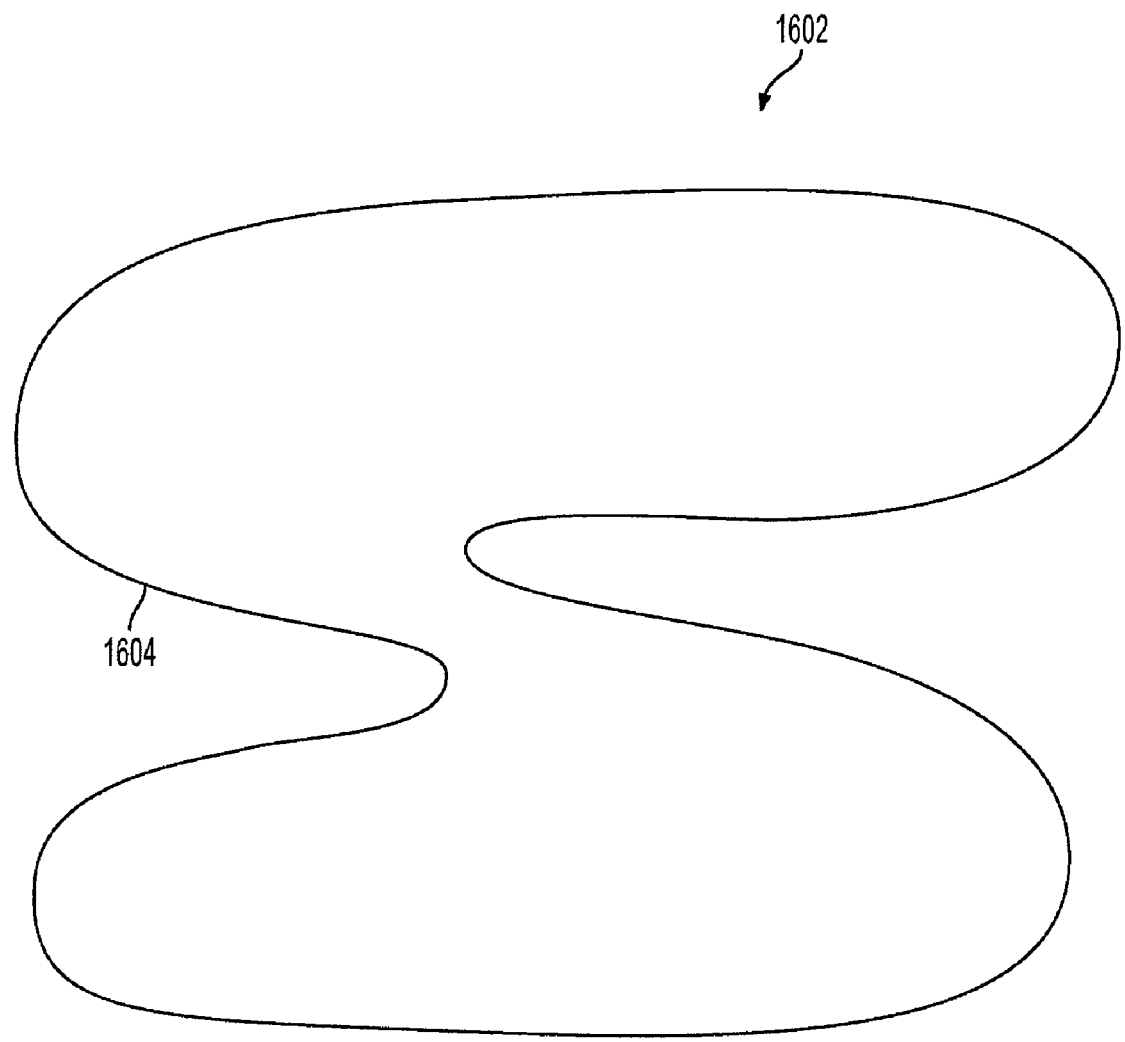
FIG. 16 is a view of an S-shaped cage with a hollow channel according to an embodiment of the invention.

FIG. 16 is a view of an S-shaped cage with a hollow channel. The S-shaped cage 1602 has a wide opening 1604. The opening 1604 has a diameter wider than the lumen on the intestine in order to prevent obstruction. The cage 1602 is a tubular cage and is made of self-expanding wire as described above, and can be covered with ePTFE, Dacron, or silicone. Alternatively, the cage 1602 can be a silicone cage that is air or silicone filled and has an injection port. The cage 1602 is not limited to an "S" shape, and can be in any spiral shape such as an "M" shape or "Z" shape. In an embodiment, the S-shaped cage can be a spiral cage which can slow down the food and induce satiety by occupying volume.

Figure 17:
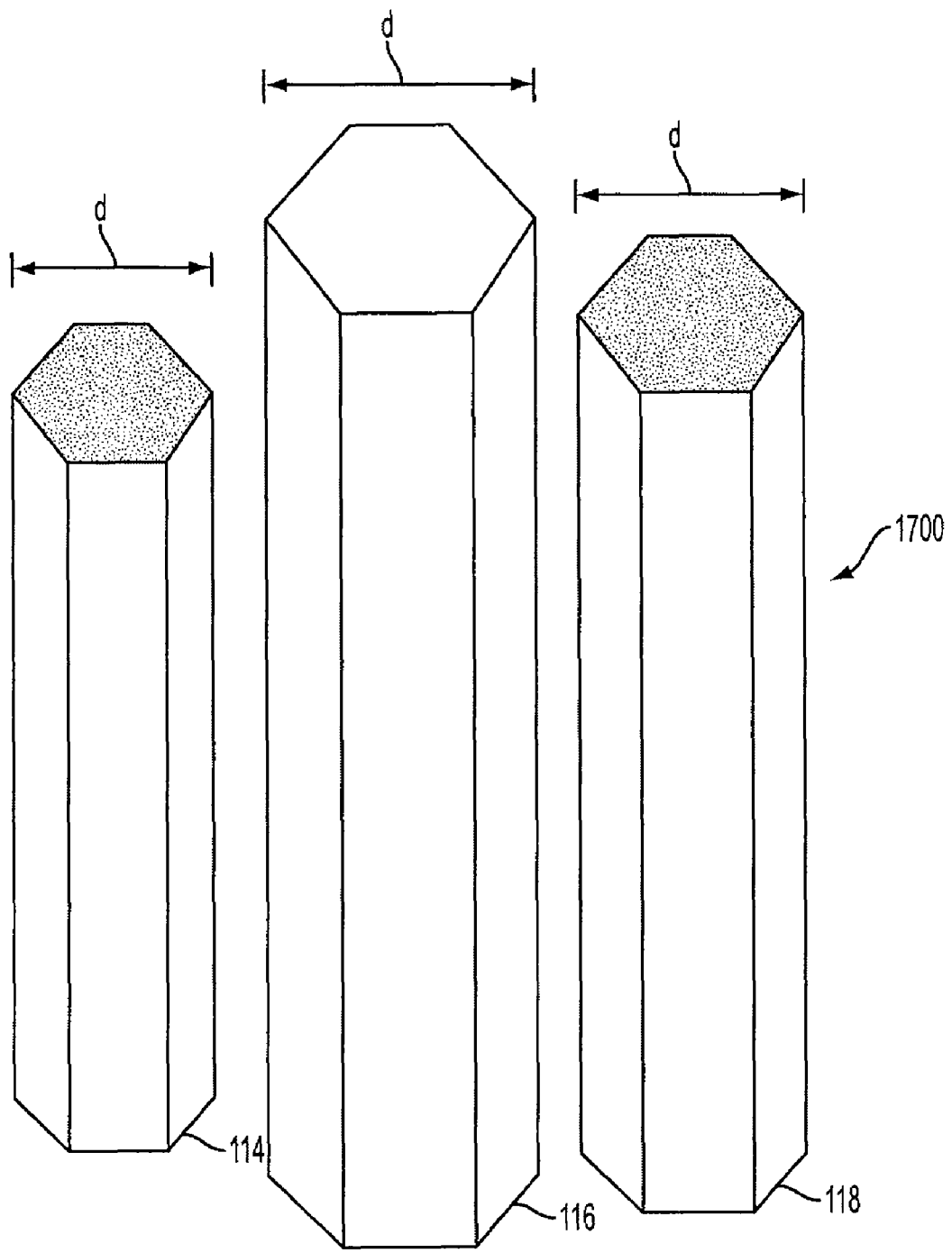
FIG. 17 is a view of unconnected hexagonal-shaped cages that make up a triple-cage device according to an embodiment of the invention.

FIG. 17 is a view of unconnected hexagonal-shaped cages that make up a triple-cage device 1700. In this embodiment, the three cages have similar dimensions as the first cage 114, the second cage 116, and the third cage 118, respectively shown in FIG. 5. However, the cages are hexagonal-shaped and have six sides instead of a round cylindrical shape.

Figure 18:
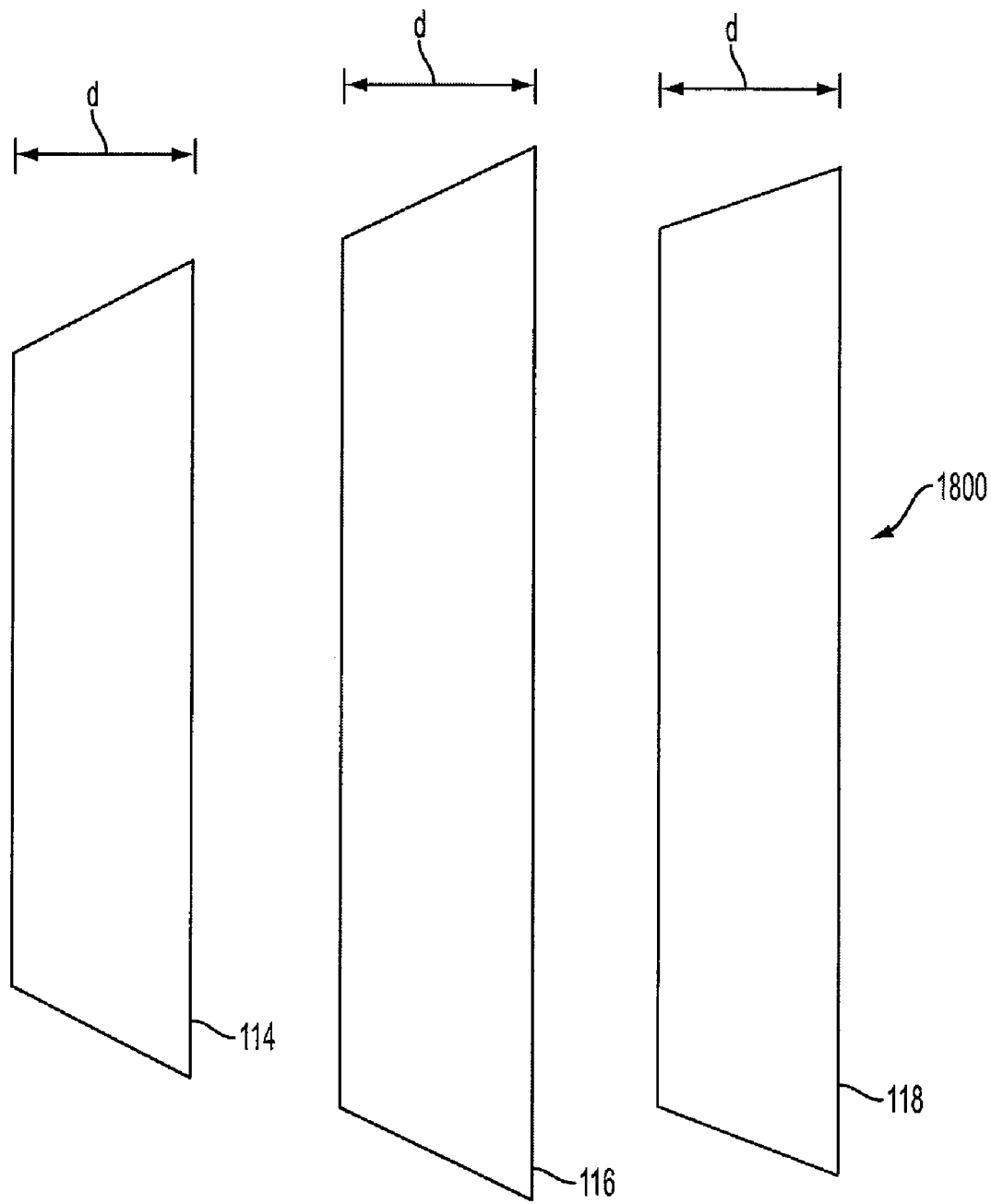
FIG. 18 is a view of unconnected vest-shaped cages that make up a triple-cage device according to an embodiment of the invention.

FIG. 18 is a view of unconnected vest-shaped cages that make up a triple-cage device 1800. In this embodiment, the three cages have similar dimensions as the first cage 114, the second cage 116, and the third cage 118, respectively shown in FIG. 5. However, the cages each have a vest shape instead of a round cylindrical shape.

Figure 19:
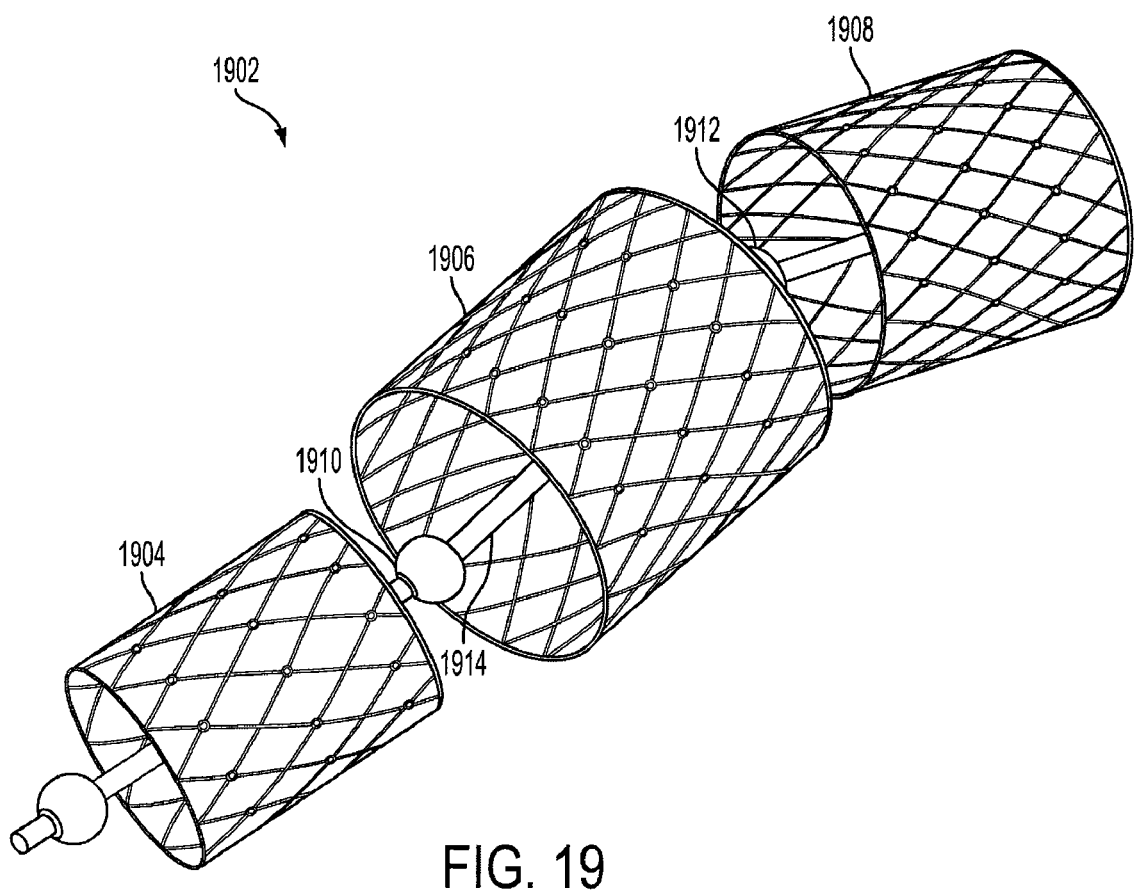
FIG. 19 is a view of a triple-cage with a central spine according to an embodiment of the invention.

FIG. 19 is a view of a triple-cage 1902 with a central spine 1914. The triple-cage device 1902 has a lower cage 1904 that is positioned near the distal stomach. The lower cage 1904 is connected to a central cage 1906 via a ball and socket joint 1910. The central cage 1906 is larger in volume than the lower cage 1904, and is connected to an upper cage 1908 via a ball and socket joint 1912. The upper cage 1908 is larger in volume than the lower cage 1904, but is smaller in volume than the central cage 1906. The upper cage 1908 is positioned in the upper stomach near the fundus. The ball and socket joints 1910 and 1912 allow angulations in the central spine 1914 so that the triple cage device 1902 can bend to accommodate various stomach sizes and shapes.

In an embodiment, the lower cage 1904 can occupy up to 0.3 L (300 cubic centimeters) of volume within the stomach body. In a preferred embodiment, the lower cage 1904 is designed to occupy approximately 200 cubic centimeters of volume within the stomach body. The lower cage 1904 can have a length of between approximately 3 centimeters and 15 centimeters, and in a preferred embodiment, can have a length of approximately 7 centimeters. The diameter of the lower cage 1904 can be between approximately 3 centimeters and 10 centimeters. In a preferred embodiment, the diameter of the lower cage 1904 is approximately 6 centimeters.

In an embodiment, the central cage 1906 can occupy between approximately 0.1 L (500 cubic centimeters) and 0.8 L (800 cubic centimeters) of volume within the stomach body. In a preferred embodiment, the central cage 1906 is designed to occupy approximately 500 cubic centimeters of volume within the stomach body. The central cage 1906 can have a length of between approximately 5 centimeters and 20 centimeters, and in a preferred embodiment, can have a length of approximately 9 centimeters. The diameter of the central cage 1906 can be between approximately 3 centimeters and 10 centimeters. In a preferred embodiment, the diameter of the central cage 1906 is approximately 8 centimeters.

In an embodiment, the upper cage 1908 can occupy up to approximately 0.3 L (300 cubic centimeters) of volume within the stomach body. In a preferred embodiment, the upper cage 1908 is designed to occupy approximately 250 cubic centimeters of volume within the stomach body. In a preferred embodiment, the entire triple-lantern device is designed to occupy up to approximately 1.03 L of volume within the stomach body.

Figure 20:
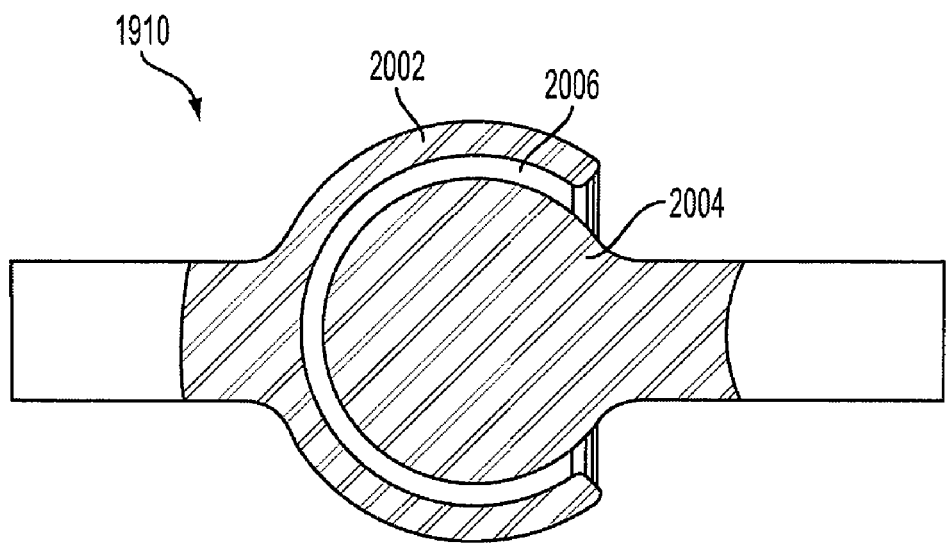
FIG. 20 is a view of a snap-locking ball and socket joint according to an embodiment of the invention.

FIG. 20 is a view of a snap-locking ball and socket joint 1910. The joint 1910 includes a socket member 2002 and a ball member 2004. The joint 1910 is secured by placing the ball member 2004 into a hollow cavity 2006 within the socket member 2002. The ball member 2004 is retained within the hollow cavity 2006 since it is sized slightly smaller than the opening of the hollow cavity 2006.

Figure 21:
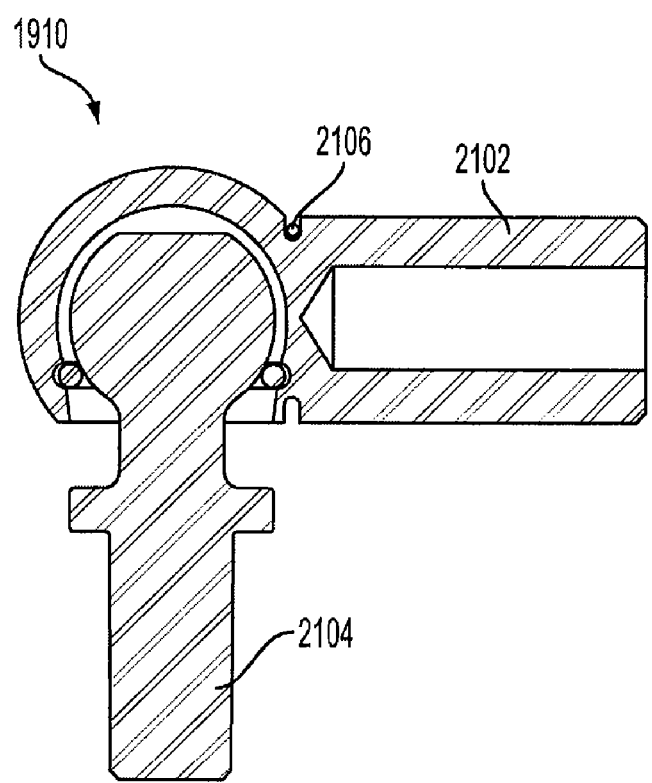
FIG. 21 is a view of a spring-loaded ball and socket joint according to an embodiment of the invention.

Alternatively, a spring-loaded ball and socket joint can be used to connect the cages. FIG. 21 is a view of a spring-loaded ball and socket joint. The socket member 2102 includes a spring 2106. The spring 2106 is actuated when the ball member 2104 is inserted into the socket member 2102, and secures the ball member 2104 within the socket member 2102.

In another embodiment (not shown), the joint has a claw member and a ball member. The claw member has fingers, claws, or spaced grips which securely hold a ball member in place, while at the same time, allows the ball member to freely rotate within the claw member. The claw member can release the ball member upon the spine of the cage being pulled, by an endoscopic retrieval device. The pull/release mechanism can be a string, cord, spring, or any other means which provides a pulling pressure.

The means to connect the cages are not limited to the ball and socket designs shown in FIGS. 20 and 21, and can be any type of connecting mechanism which allows the central spine to bend so that the triple-cage device can accommodate various sized and shaped stomachs.

Furthermore, the lanterns are not limited to the circular or cylindrical shape shown in FIG. 19, and can be any geometric shape as described above for the lantern-shaped cage 1002.

Figure 22:
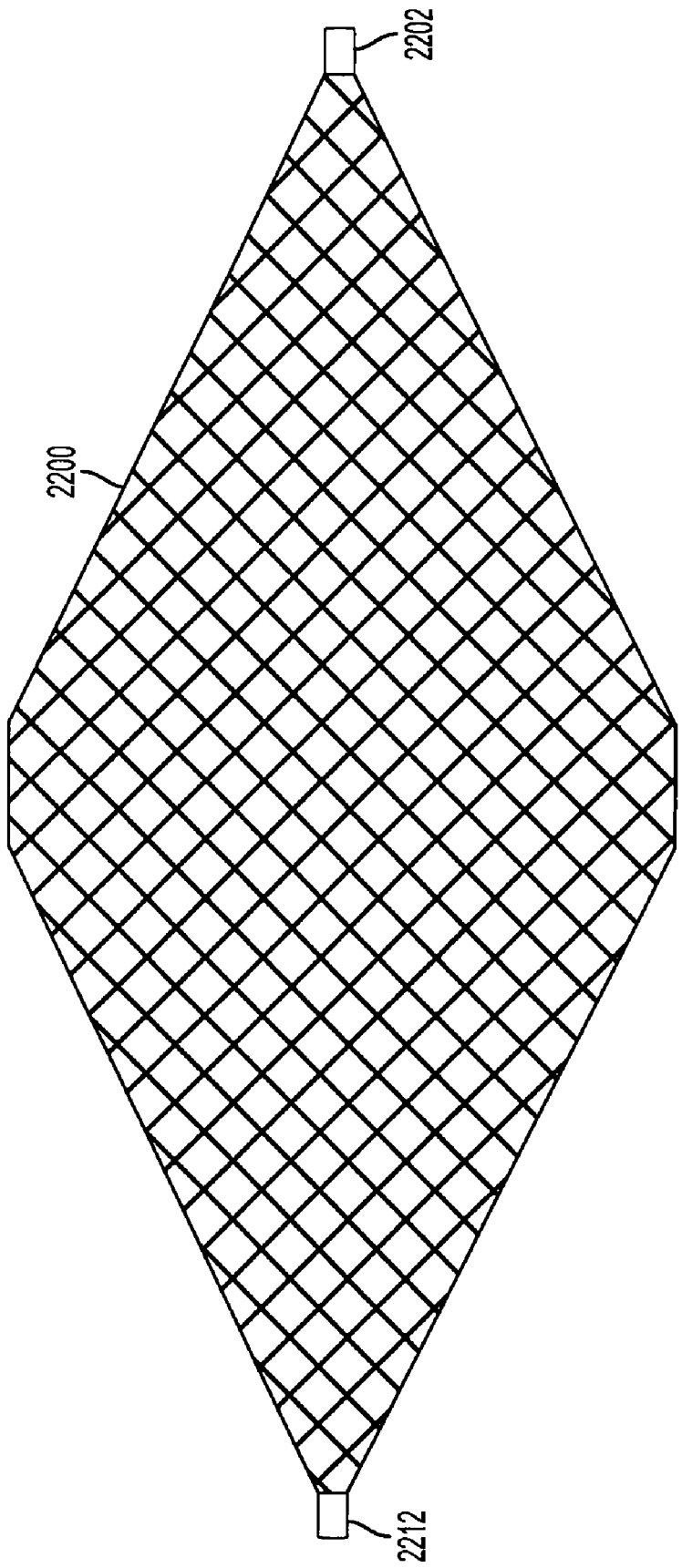
FIG. 22 is a view of a diamond-shaped cage device according to an embodiment of the invention.

FIG. 22 is a view of a diamond-shaped cage device according to an embodiment of the invention. The device is covered with a covering 2200, which is preferably made from an elastomeric material, such as ePTFE, Dacron®, or silicon. Alternatively, the covering 2200 can be made from any flexible material which is biocompatible with the human body. The covering 2200 is connected to a first outer rod 2202 and a second outer rod 2212 by sutures, staples, adhesives such as the DYMAX MD® "1000", "CTH" and "MSK" series adhesives that cure within seconds upon exposure to UV and visible light and permit bonding of elastomeric materials, or any other method or mechanism that can secure the covering 2200 to the outer rods 2202 and 2212. The covering 2200 forms an air-tight, non-permeable, leak-proof seal with the outer rods 2202 and 2212 to prevent air, liquid, food, and other matter from entering inside the diamond-shaped cage device. In an embodiment, the covering 2200 is also sutured, stapled or adhesively attached to other parts of the device, such as internal support structures (not shown).

Figure 23:
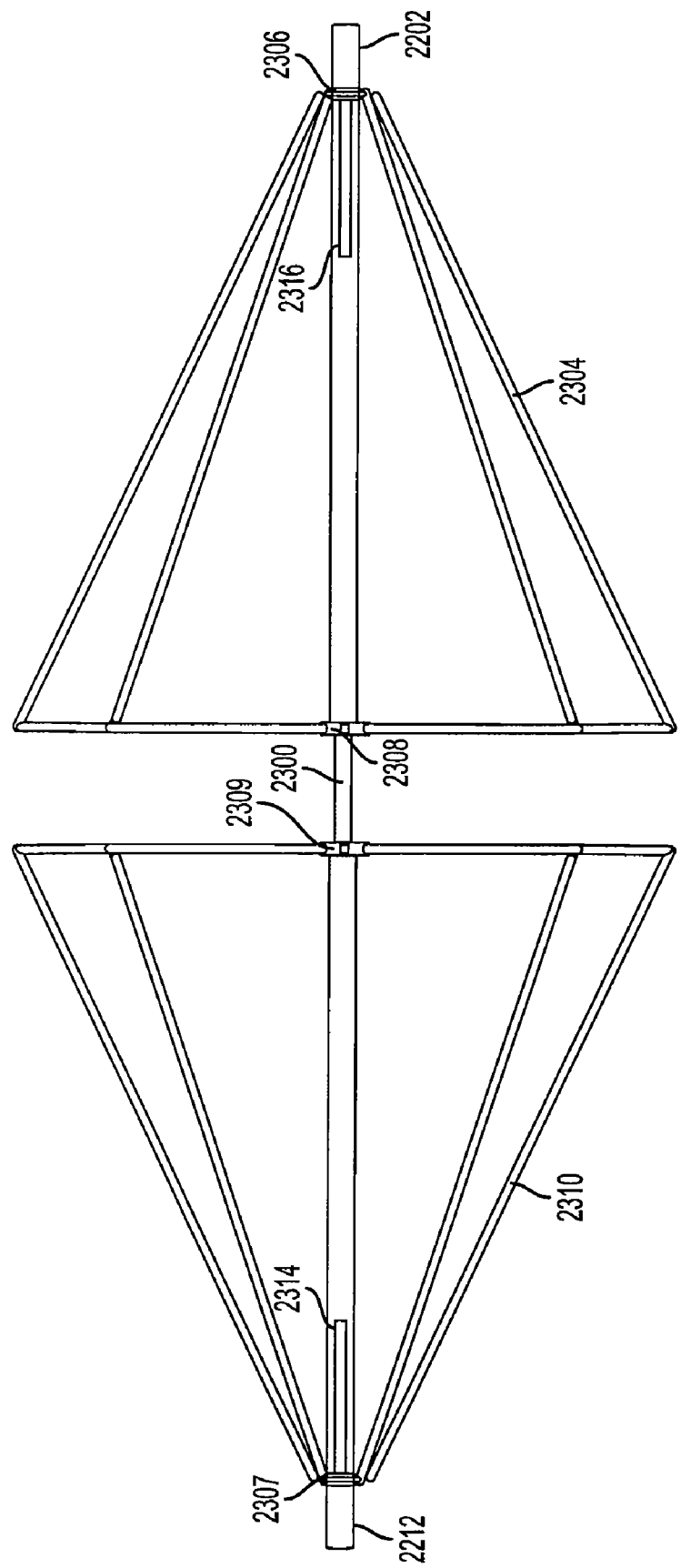
FIG. 23 is a view of fully-extended support structures of a diamond-shaped cage device according to an embodiment of the invention.

FIG. 23 is a view of fully-extended support structures of a diamond-shaped cage device according to an embodiment of the invention. In an embodiment, the diamond-shaped cage comprises a first structure 2304 which faces and is adjacent to a second structure 2310. The structures 2304 and 2310 may be made of a wire mesh. The structures 2304 and 2310 or wire mesh preferably being made of nickel titanium (Nitinol), stainless steel, aluminum, tungsten, copper, gold, cobalt chromium, other alloys and PEEK material or other polymer materials. In an embodiment, the diamond-shaped cage device is made of a self-expanding wire mesh. The wire mesh can have a diameter of approximately 1/1000th of an inch to approximately 100/1000th of an inch. In a preferred embodiment, the wire mesh preferably has a diameter of approximately 20/1000th of an inch.

Figure 24:
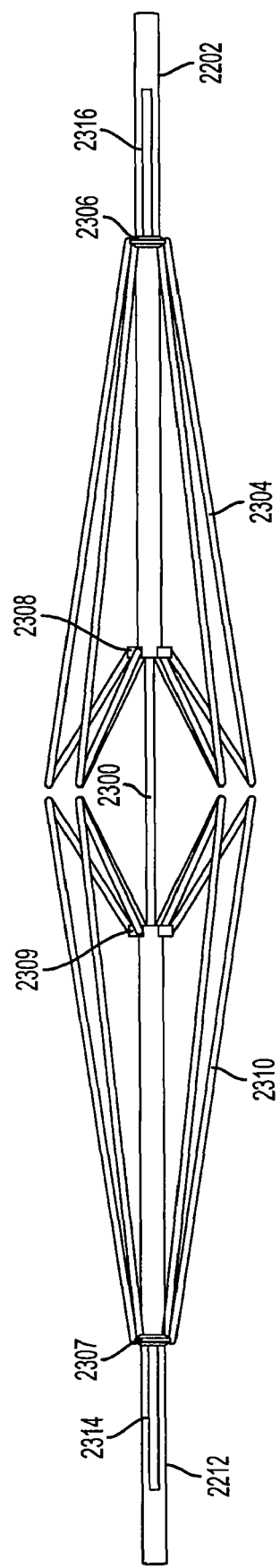
FIG. 24 is a view of collapsed support structures of a diamond-shaped cage device according to an embodiment of the invention.

The cage device includes a first outer rod 2202 and a second outer rod 2212. The first support structure 2304 is connected to the first outer rod 2202 via a first connector 2306 and a second connector 2308. Similarly, the second support structure 2310 is connected to the second outer rod 2212 via a first connector 2307 and a second connector 2309. In an embodiment, to collapse the cages, the first and second outer rods 2202 and 2212 are pulled outwards and the first and second support structures 2304 and 2310 fold into a collapsed position as shown in FIG. 24. When the first outer rod 2202 is pulled in a direction away from the second outer rod 2212, and the movement of the first outer rod 2202 causes the first support structure 2304 to fold downward and inward. Similarly, when the second outer rod 2212 is pulled in a direction away from the first outer rod 2202, and the movement of the second outer rod 2212 causes the second support structure 2310 to fold downward and inward.

The first outer rod 2202 and the second outer rod 2212 are movable along a central inner rod 2300. In an embodiment, the first outer rod 2202 includes a first channel 2316, and the second outer rod 2212 includes a second channel 2314. The first connecter 2306 is connected to the inner rod 2300 through the first channel 2316, and the second connector 2308 is connected to the first outer rod 2202. In a fully-extended position, the first connector 2306 contacts the first channel 2316 at a side of the first channel 2316 farthest away from the second support structure 2310. Similarly, the first connecter 2307 is connected to the inner rod 2300 through the second channel 2314, and the second connector 2309 is connected to the second outer rod 2212. The inner rod 2300 fits into the first outer rod 2202 and the second outer rod 2212 so there is little space between the rods to allow the inner rod 2300 to slide within the outer rods 2202 and 2212.

When the first outer rod 2202 is pulled in a direction away from the second outer rod 2212, the first connector 2306 remains in a fixed position as it is connected to the inner rod 2300 while the second connector 2308 moves with the first outer rod 2202, as it is connected to the first outer rod 2202.

Likewise, the second support structure 2310 is collapsed in a similar fashion when the second outer rod 2212 is pulled in a direction away from the first outer rod 2202. The second outer rod 2212 is moved in a direction away from the first outer rod 2202 along the inner rod 2300, causing the second support structure 2310 to fold downward and inward as shown in FIG. 24.

FIG. 24 is a view of collapsed support structures of a diamond-shaped cage device according to an embodiment of the invention. In an embodiment, applying pressure to one of the outer rods causes both of the support structures to collapse. In a collapsed position, the first connector 2306 contacts the first channel 2316 at a side of the first channel 2316 closest to the second support structure 2310. In another embodiment, to retrieve the cage device into a sheath, pressure applied to the support structure from the sheath entrance causes the device to collapse so that it can fit into the sheath for retrieval. In another embodiment, when pressure is applied to the first outer rod 2202, the first support structure 2304 and the second support structure 2310 both fold downward and inward. The first outer rod 2202 can have an actuating mechanism which causes or triggers the second outer rod 2212 to move in a direction away from the first outer rod 2202 upon an exertion of pressure to the first outer rod 2202.

Figure 25:
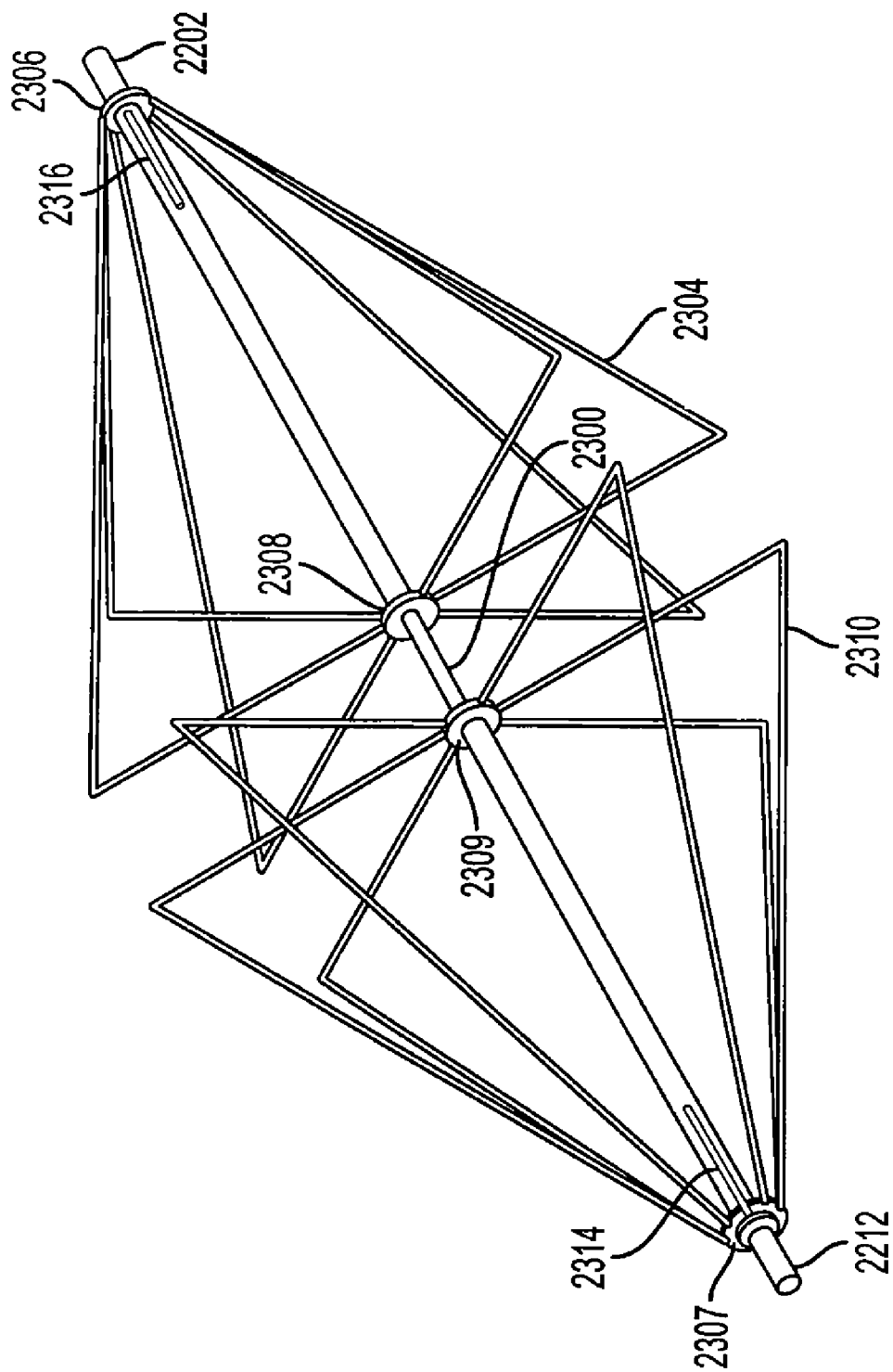
FIG. 25 is a perspective view of fully-extended support structures of a diamond-shaped cage device according to an embodiment of the invention.

FIG. 25 is a perspective view of fully-extended support structures of a diamond-shaped cage device according to an embodiment of the invention. The diamond-shaped cage has multiple support structures which form the support structures of the cage device. In an embodiment, the cage device can have from two to ten support structures. In a preferred embodiment, the cage device has at least six support structures. In another embodiment, the support structures can be shaped in the form of a square, triangle, semi-circle, or any other geometric shape.

Figure 26:
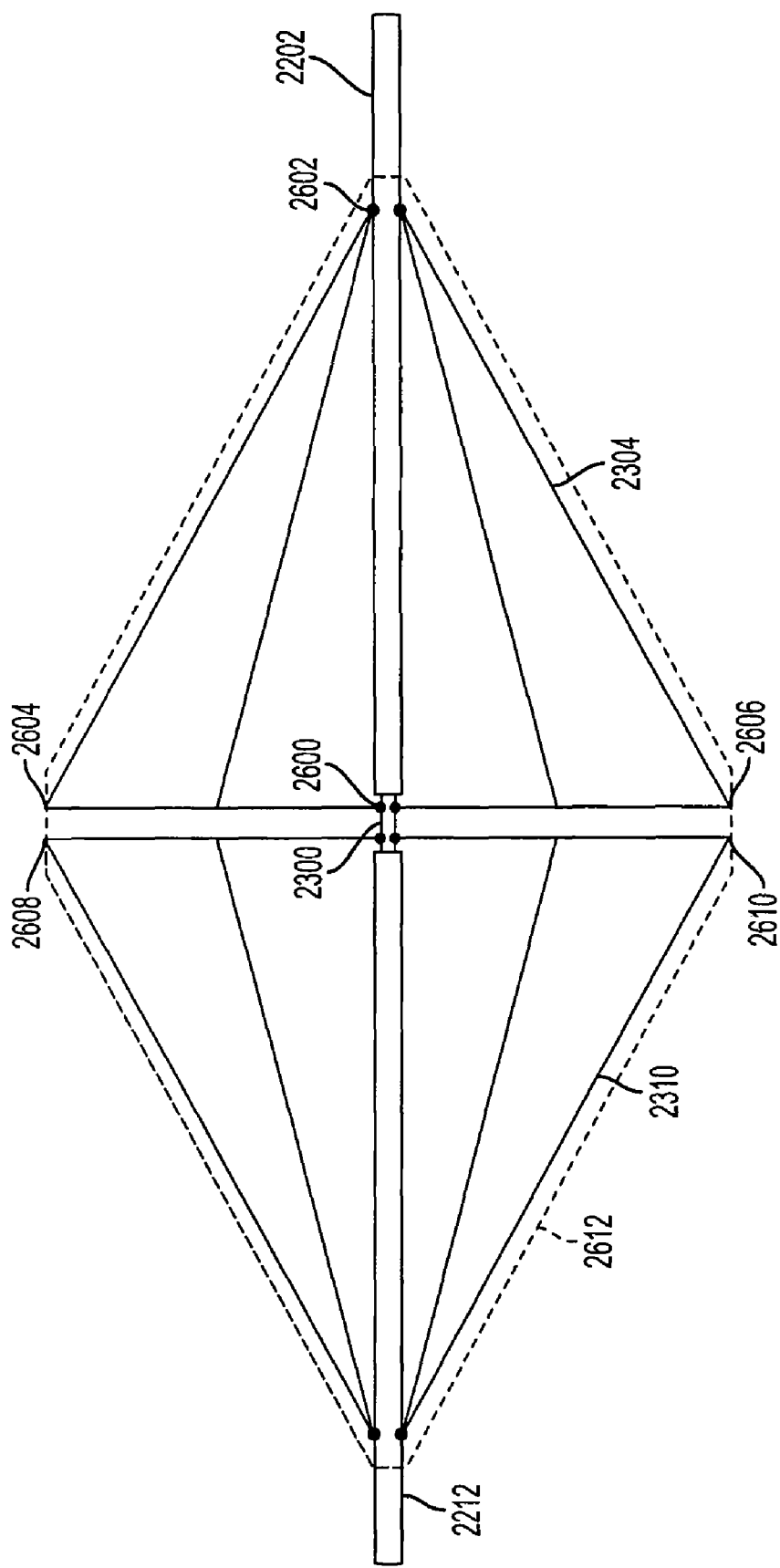
FIG. 26 is a view of fully-extended support structures of a diamond-shaped cage device according to an embodiment of the invention.
Figure 27:
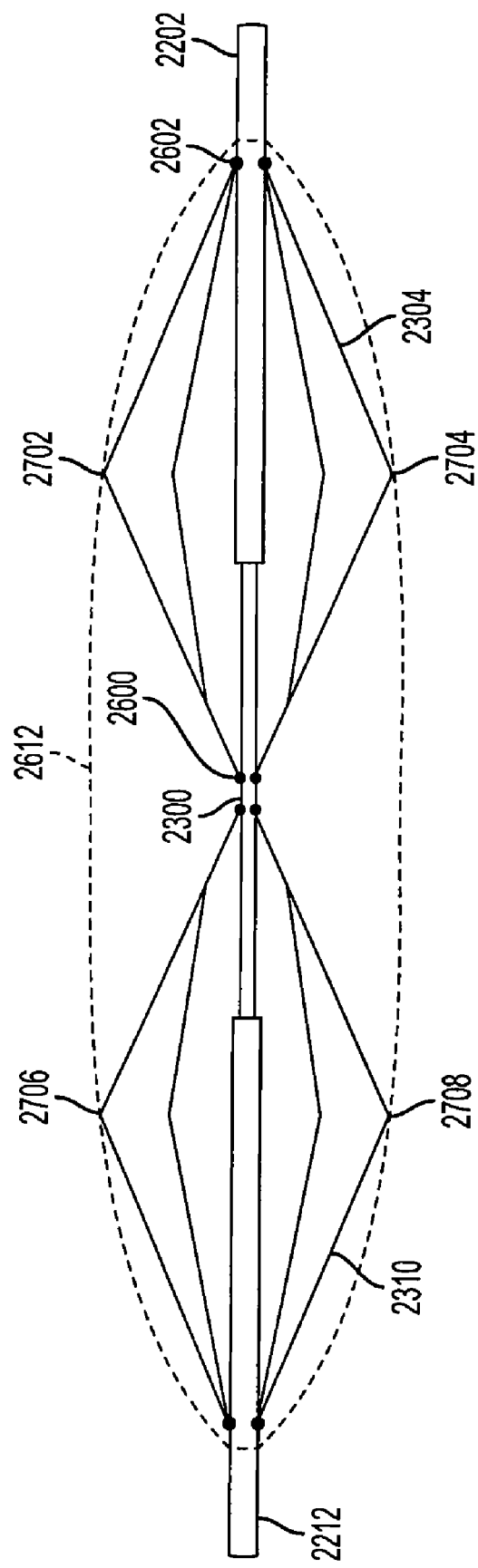
FIG. 27 is a view of semi-extended support structures of a diamond-shaped cage device according to an embodiment of the invention.

FIG. 26 is a view of fully-extended support structures of a diamond-shaped cage device according to an embodiment of the invention. In this embodiment, the first support structure 2304 is attached to the inner rod 2300 at anchor 2600. The first support structure 2304 is connected to the first outer rod 2202 at anchor 2602. The first outer rod 2202 and the second outer rod 2212 can provide support to the support structures as they are adjacent to the inner anchors when the cage device is in a fully-extended position. When the first outer rod 2202 is pulled in a direction away from the second outer rod 2212, or when pressure is applied to the first outer rod 2202, the first support structure 2304 is collapsed downward and inward, as shown in FIG. 27.

Figure 28:
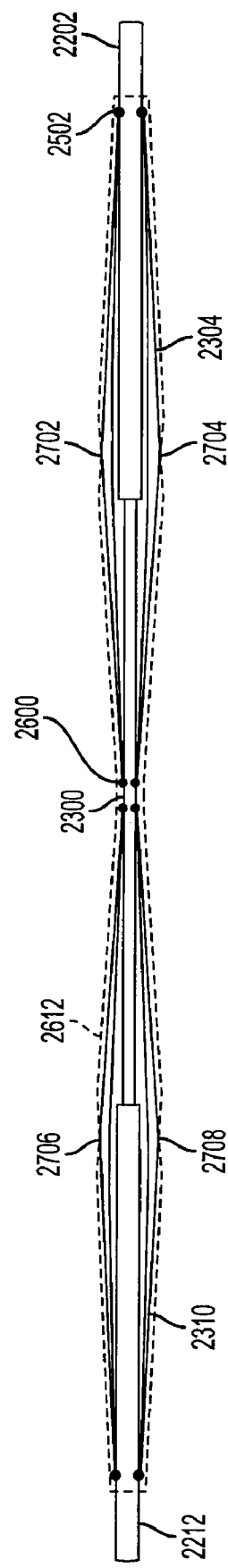
FIG. 28 is a view of collapsed support structures of a diamond-shaped cage device according to an embodiment of the invention.

In a fully-extended position, the first outer rod 2202 and the second outer rod 2212 are locked into position by at least one locking mechanism (not shown) which prevents movement of the rods 2202 and 2212. The locking mechanism can be a pin, wedge, or ball and groove system that secures the outer rods 2202 and 2212 to the inner rod 2300 which prevents the rods from moving until a certain amount of pressure is applied. The locking mechanisms can be connected to the outer rods, or alternatively, placed along the inner rod 2300. In another embodiment, the first outer rod 2202 and the second outer rod 2212 can be locking into position by at least one locking mechanism when the outer rods are in the collapsed position. The first and second outer rods 2202 and 2212 are movable between a first position where the support structures 2304 and 2310 are in a fully-extended position (FIG. 26), a second position where the support structures 2304 and 2310 are in a partially-collapsed position (FIG. 27), and a third position where the support structures 2304 and 2310 are in a fully-collapsed position (FIG. 28).

In an embodiment, a covering 2612, similar to the covering 2200 described above, covers the entire cage device, including both the first support structure 2304 and the second support structure 2310. The covering 2612 is preferably made from an elastomeric material, such as ePTFE, Dacron®, or silicon, and can be knitted to form a cloth. Alternatively, the covering 2612 can be made from any flexible material which is biocompatible with the human body. The covering 2612 may be connected to the first support structure 2304 at a first connection point 2604 and a second connection point 2606. The covering 2612 is connected to the second support structure 2310 at a first connection point 2608 and a second connection point 2610. The covering 2612 is also connected to the first outer rod 2202 and the second outer rod 2212 to form an air-tight, non-permeable, leak-proof seal that prevents air, liquid, food, and other matter from entering the diamond-shaped cage device. The covering 2612 can be connected to the cage device with sutures, staples, adhesives, or any other method or mechanism that can secure the covering 2612 to the outer rods 2202 and 2212 and the support structures 2304 and 2310. In an embodiment, the covering 2612 is also sutured, stapled or adhesively attached to other parts of the device, such as internal support structures (not shown).

In an embodiment, the cage device can have multiple locking positions (e.g., can be locked in the first, second, and third positions described above) and is adjustable, allowing a physician or healthcare professional to expand the cage device to a desired size. For example, FIG. 27 is a view of semi-extended support structures of a diamond-shaped cage device according to an embodiment of the invention. In the semi-extended position, the cage device is only partially expanded to accommodate a smaller sized stomach or in order to provide less fullness in the patient's stomach.

In FIG. 27, the covering 2612 is attached the first support structure 2304 at a first connection point 2702 and a second connection point 2704. The covering 2612 is attached to the second support structure 2310 at a first connection point 2706 and a second connection point 2708. The covering 2612 is also connected to the first outer rod 2202 and the second outer rod 2212 to form an air-tight, non-permeable, leak-proof seal that prevents air, liquid, food, and other matter from entering the diamond-shaped cage device.

FIG. 28 is a view of collapsed support structures of a diamond-shaped cage device according to an embodiment of the invention. In the collapsed position, the cage device can be inserted into a sheath for deployment into the stomach or retrieval from the stomach. In the collapsed position, the cage device has a height of approximately 1 centimeter or less, and a length of approximately 11.5 centimeters or less. However, the height and width of the collapsed cage device can vary based upon the fully-extended size and dimensions of the cage device. The fully-extended size of the cage device can depend on the dimensions of the patient's stomach and the amount of volume desired to be occupied by the cage device.

In another embodiment, the cage system includes a single pyramid-shaped cage, instead of two opposing cage structures. The single cage system operates in the same or similar manner as the diamond-shaped cage device described above. In another embodiment, the single cage device has a lantern shape or a cylindrical shape.

Figure 29:
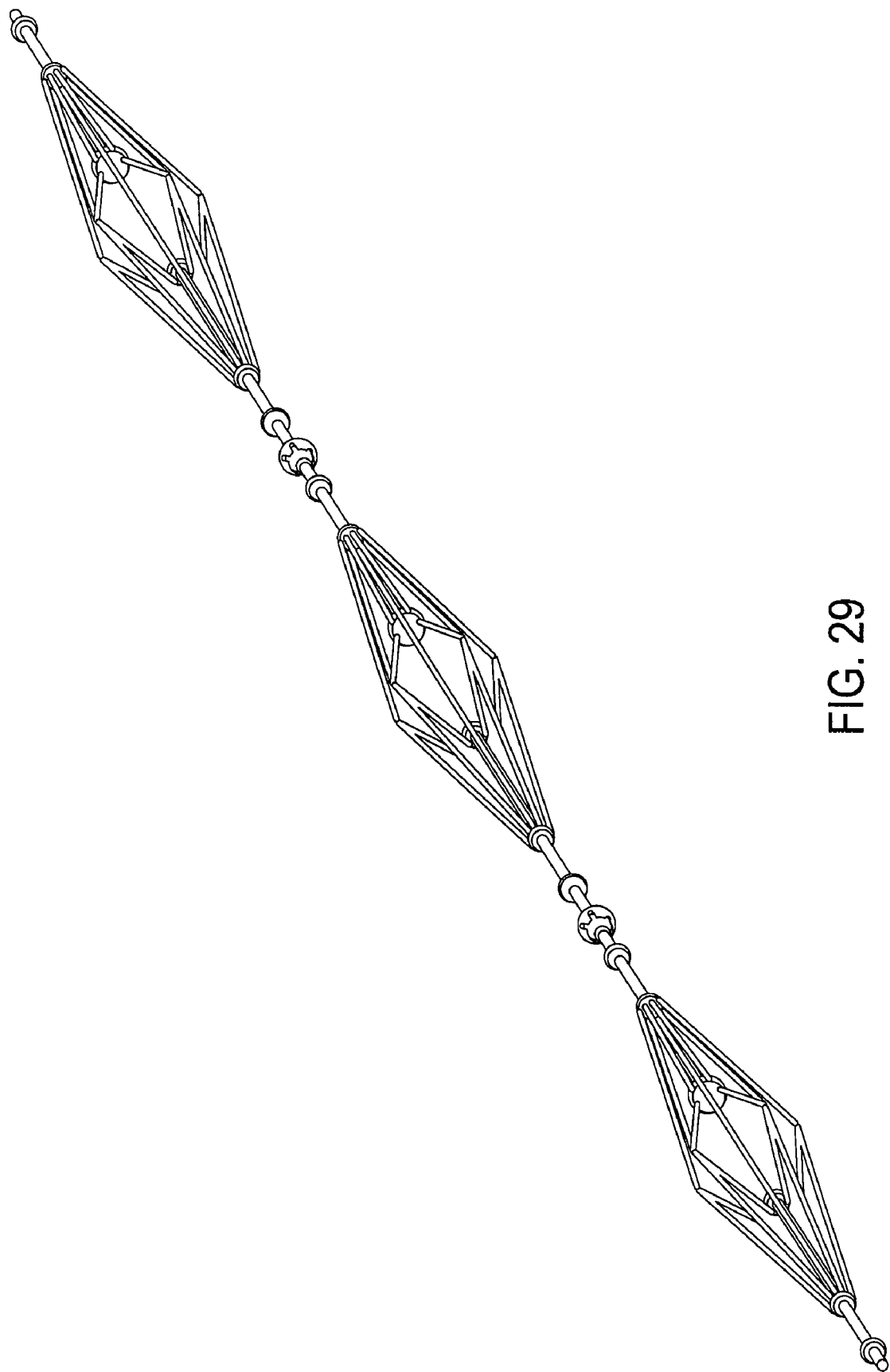
FIG. 29 is a view of a triple diamond-shaped cage device according to an embodiment of the invention.

FIG. 29 is a view of a triple diamond-shaped cage device according to an embodiment of the invention. The device includes at least three diamond-shaped cage devices connected serially. Each cage device is connected to the other in a manner similar to that shown in FIGS. 20 and 21. Alternatively, each cage device can be connected to the other using a claw member and a ball member as described above. In an embodiment, each of the three diamond-shaped cage devices can be of a varying shape and size.

In an embodiment, the single cage device or the triple cage device can be sized and dimensioned when fully or partially extended to fit snugly within the stomach so that the side walls of the stomach hold each of the cages in place. For example, after a sleeve gastrectomy procedure, a significant portion of the stomach is removed, leaving a cylindrical or sleeve-shaped stomach. The one or more cage devices can be sized and dimensioned or adjusted to fit flush against the stomach walls when the stomach size has been reduced after the gastrectomy procedure.

Figure 30:
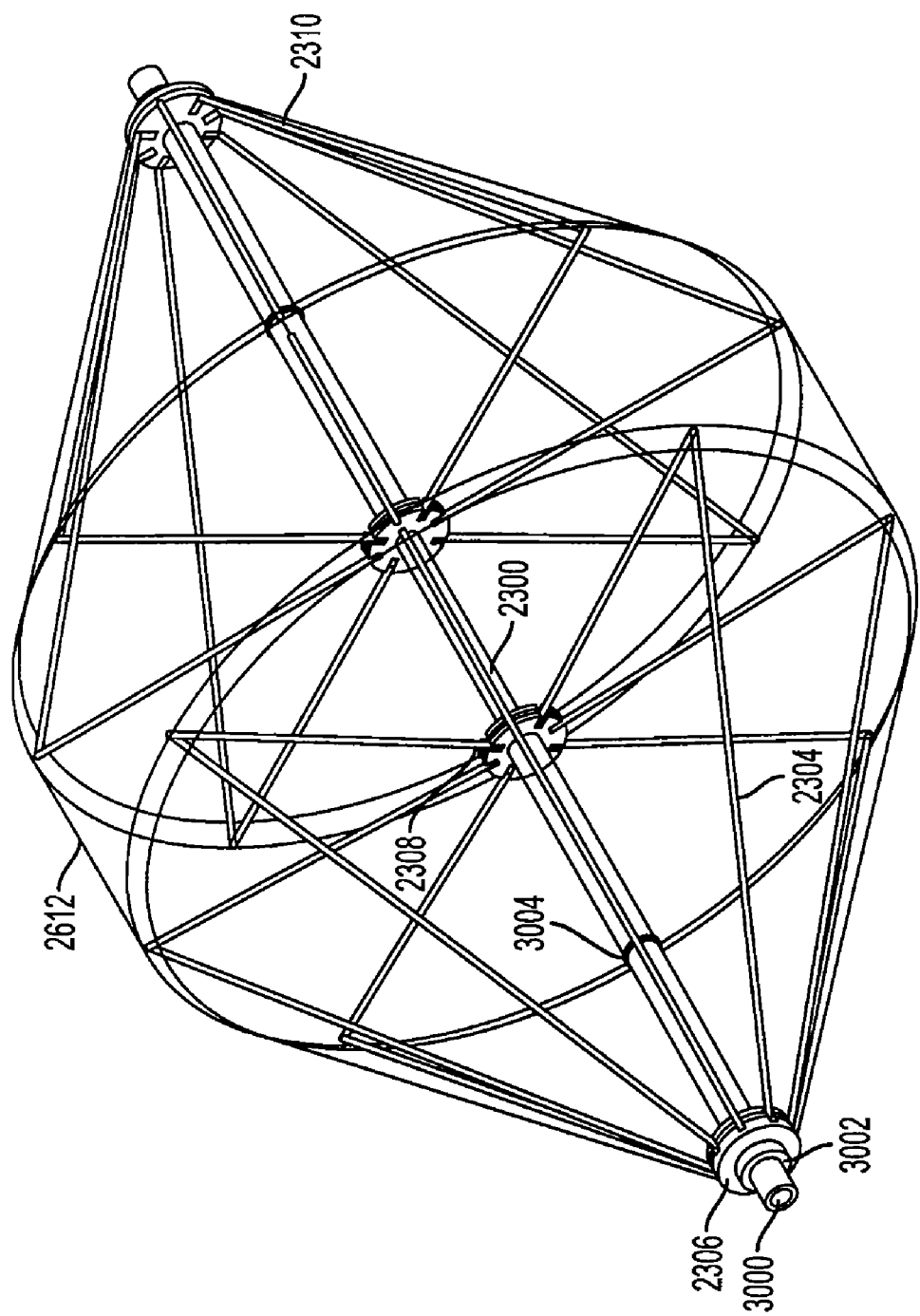
FIG. 30 is a perspective view of fully-extended support structures of a diamond-shaped cage device with a covering according to an embodiment of the invention.

FIG. 30 is a perspective view of fully-extended support structures of a diamond-shaped cage device with a covering according to an embodiment of the invention. The cage device includes a first support structure 2304 and a second support structure 2310. The first support structure has an outer rod 3000 that is movable along the central inner rod 2300. The outer rod 3000 includes a locking mechanism 3002 and a stopping mechanism 3004. The outer rod 3000 also includes a first connector 2306 and a second connector 2308. The first connector 2306 is an anchor for all of the long wires of the first support structure 2304. The second connector 2308 is an anchor for all of the shorter wires of the first support structure 2304.

When the outer rod 3000 is pulled in a direction away from the second support structure 2310, the stopping mechanism 3004 comes into contact with the first connector 2306 and prevents the outer rod 3000 from being pulled out further. Thus, the stopping mechanism 3004 restricts the size of the cage device upon collapse. In an embodiment, the stopping mechanism 3004 can be a circular or semi-circular protrusion that extends outward from the outer rod 3000. In another embodiment, the stopping mechanism 3004 can be a lip, latch, pin, button, or any other means which prevents the outer rod 3000 from extending a certain distance beyond the first connector 2306.

In an embodiment, the covering 2612 is connected directly to the first connector 2306, creating a non-permeable, air tight seal. When the cage device is in a fully-extended position, the locking mechanism 3002 is attached to the first connector 2306. The locking mechanism 3002 provides a non-permeable, air tight seal at the junction between the first connector 2306 and the outer rod 3000. Likewise, when the cage device is in a collapsed position, the stopping mechanism 3004 provides a non-permeable, air tight seal at the junction between the first connector 2306 and the outer rod 3000.

In another embodiment, the outer rod 3000 has multiple stopping mechanisms and locking mechanisms located at various positions along the outer rod 3000. The multiple stopping mechanisms and locking mechanisms allow the cage device to be collapsed, expanded and locked to different sizes and shapes.

The locking mechanism 3002 prevents the cage device from expanding further past a fully-expanded position. When the outer rod 3000 is pushed inwards toward the second support structure 2310, the locking mechanism 3002 comes into contact with the first connector 2306. The pushing pressure causes the locking mechanism 3002 to be locked and securely held into place with the first connector 2306. An exemplary locking mechanism 3002 is shown in more detail in FIG. 32.

Figure 31:
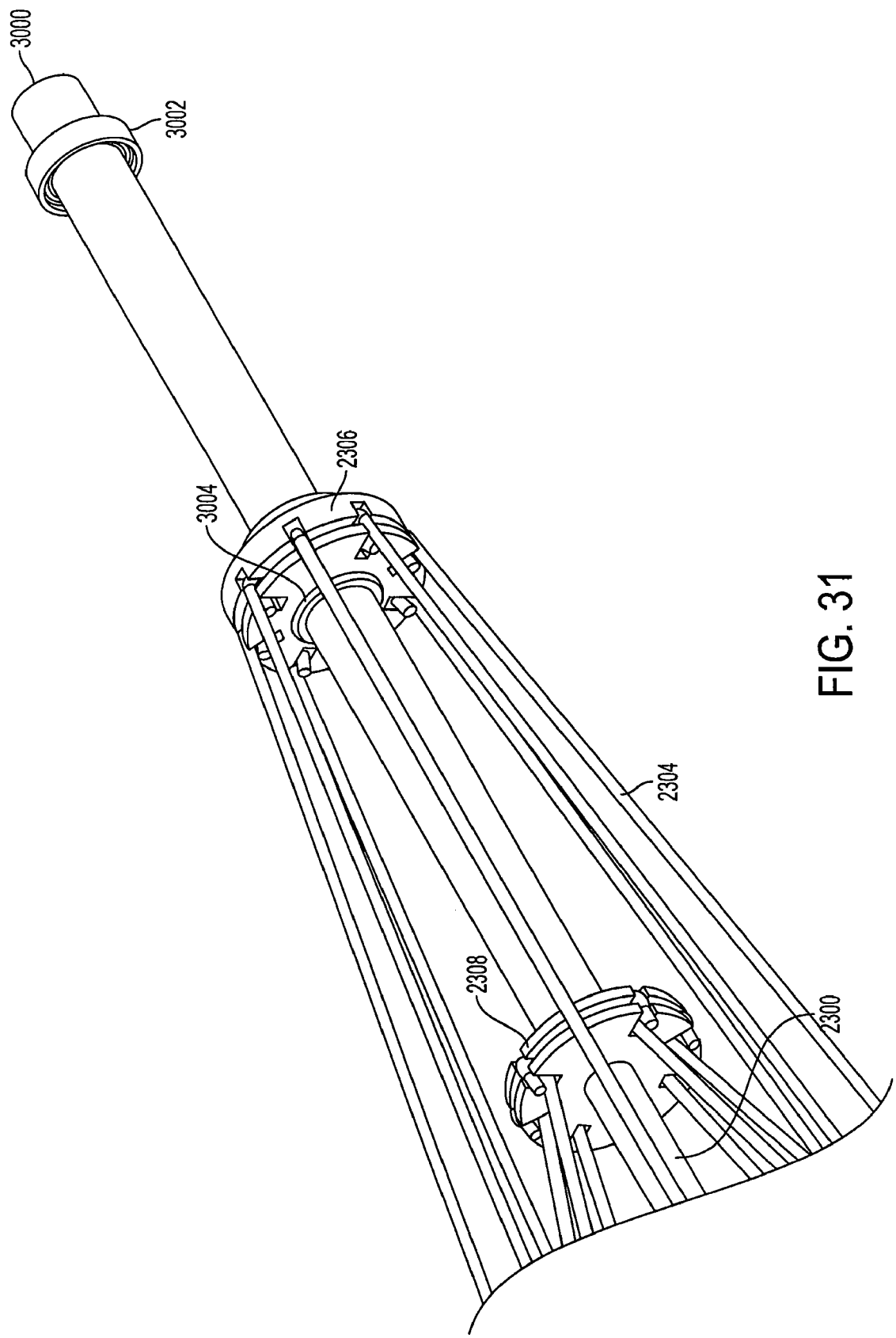
FIG. 31 is a perspective view of a portion of a collapsed support structure of a diamond-shaped cage device according to an embodiment of the invention.

FIG. 31 is a perspective view of a portion of a collapsed support structure of a diamond-shaped cage device according to an embodiment of the invention. In the collapsed position, the stopping mechanism 3004 is in contact with the first connector 2306. When the stopping mechanism 3004 comes into contact with the first connector 2306, the pulling pressure exerted on the outer rod 3000 causes the stopping mechanism 3004 to become affixed to the first connector 2306 so that the outer rod 3000 does not slide back towards the second support structure 2310. This prevents the cage device from re-expanding or opening. When the cage device is in the collapsed position, the locking mechanism 3002 is no longer in contact with the first connector 2306.

Figure 32:
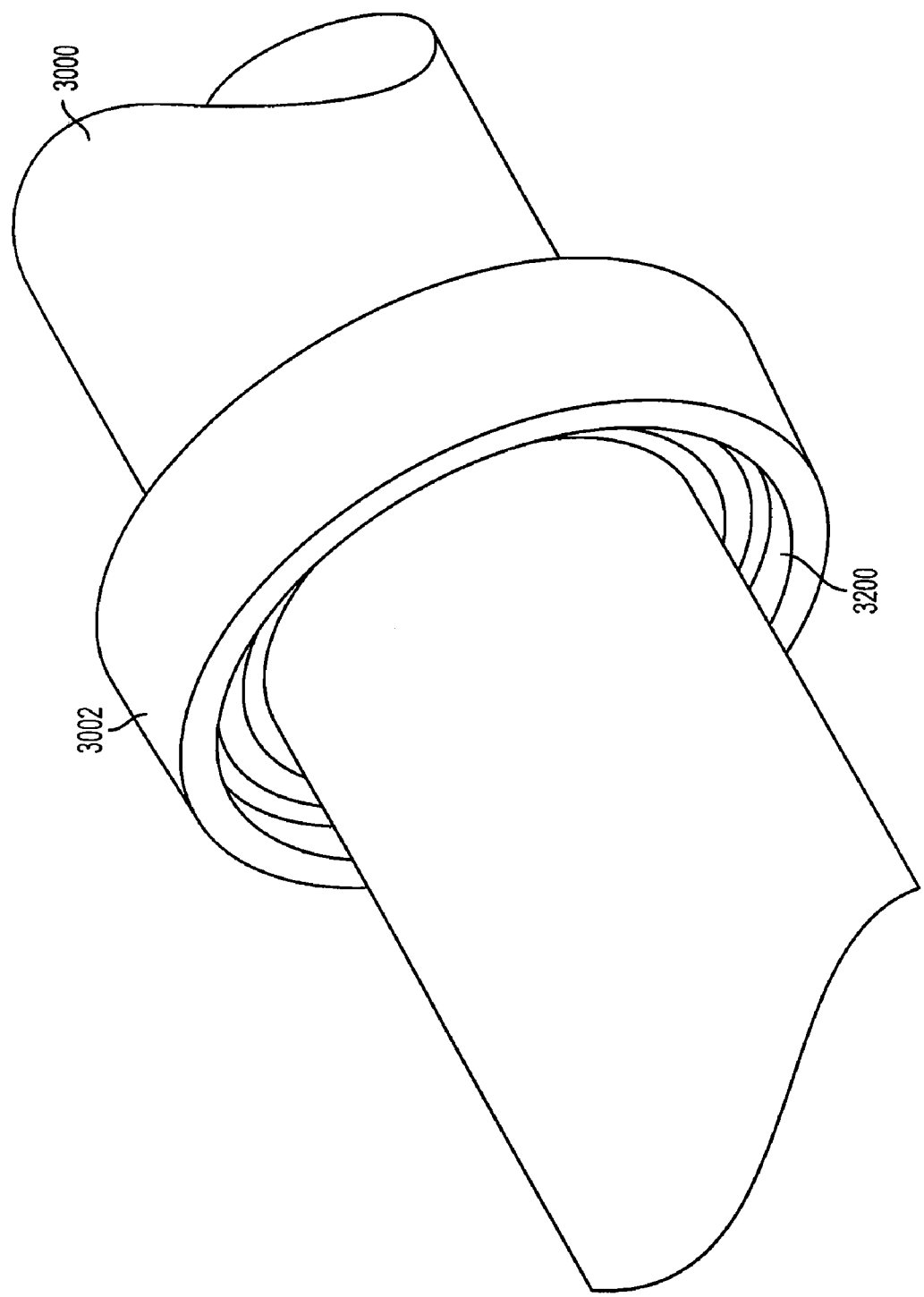
FIG. 32 is a view of a locking mechanism according to an embodiment of the invention.

FIG. 32 is a view of a locking mechanism according to an embodiment of the invention. In an embodiment, the locking mechanism 3002 is located at a fixed position on the outer rod 3000 and is permanently attached to the outer rod 3000. The locking mechanism 3002 can be made of rubber, plastic, steel, a thermoplastic material, or any other material with sufficient rigidity to lock with the outer rod 3000. In an embodiment, the inner surface 3200 of the locking mechanism 3002 has male grooves configured to lock with female grooves on a locking member (not shown) on the first connector 2306 and secures the first connector 2306 in place upon contact.

Figure 33:
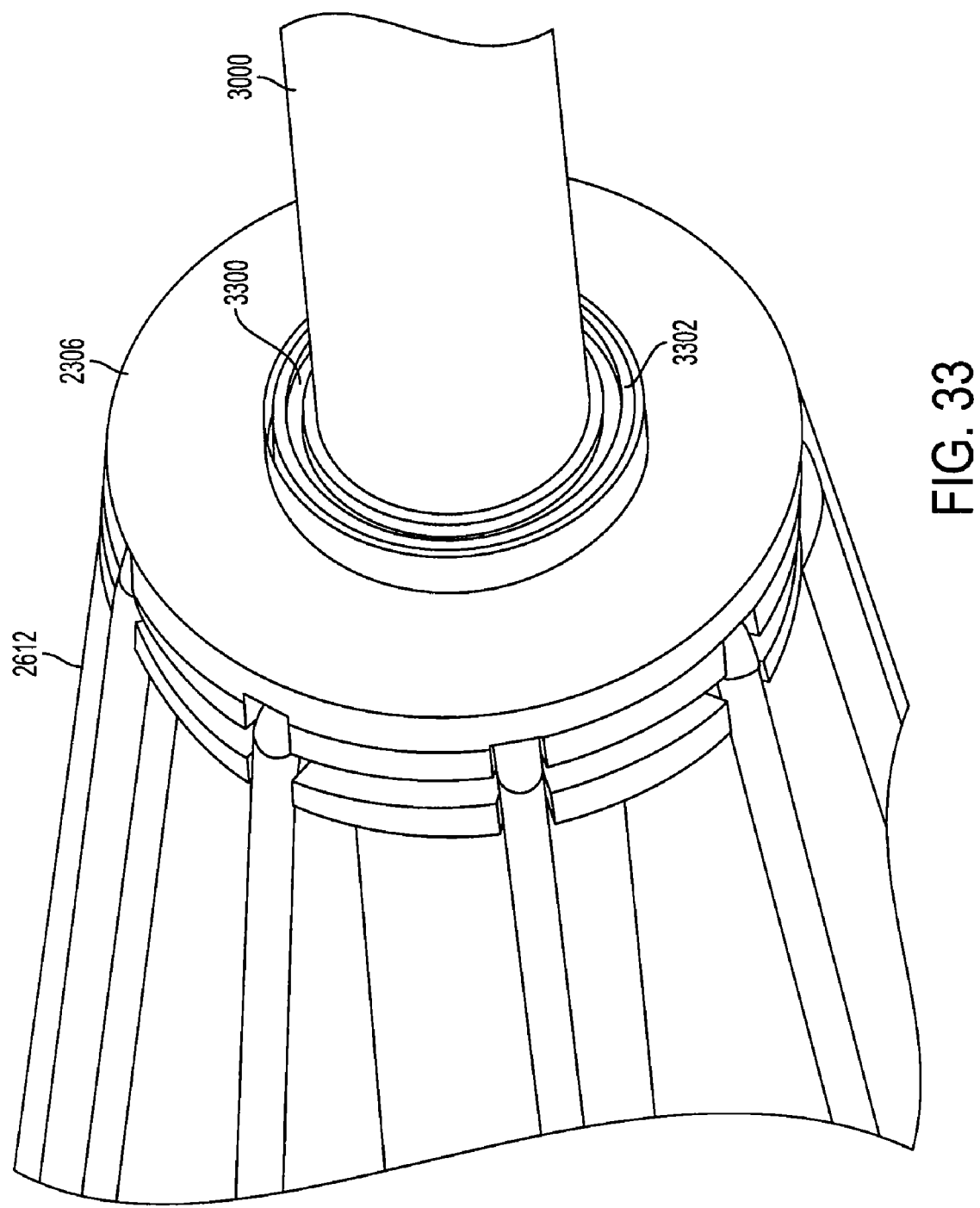
FIG. 33 is a view of a connector according to an embodiment of the invention.

FIG. 33 is a view of a connector according to an embodiment of the invention. The first connector 2306 has a locking member 3300 which is designed to receive the locking mechanism 3002. The inner surface 3302 of the locking member 3300 has female grooves which align and lock with the male grooves of the inner surface 3200 of the locking mechanism 3002. In another embodiment, the inner surface 3302 and the inner surface 3200 can have button grooves, pins, interlocking teeth, or any other type of design which allows the two surfaces to lock with each other upon contact.

Figure 34:
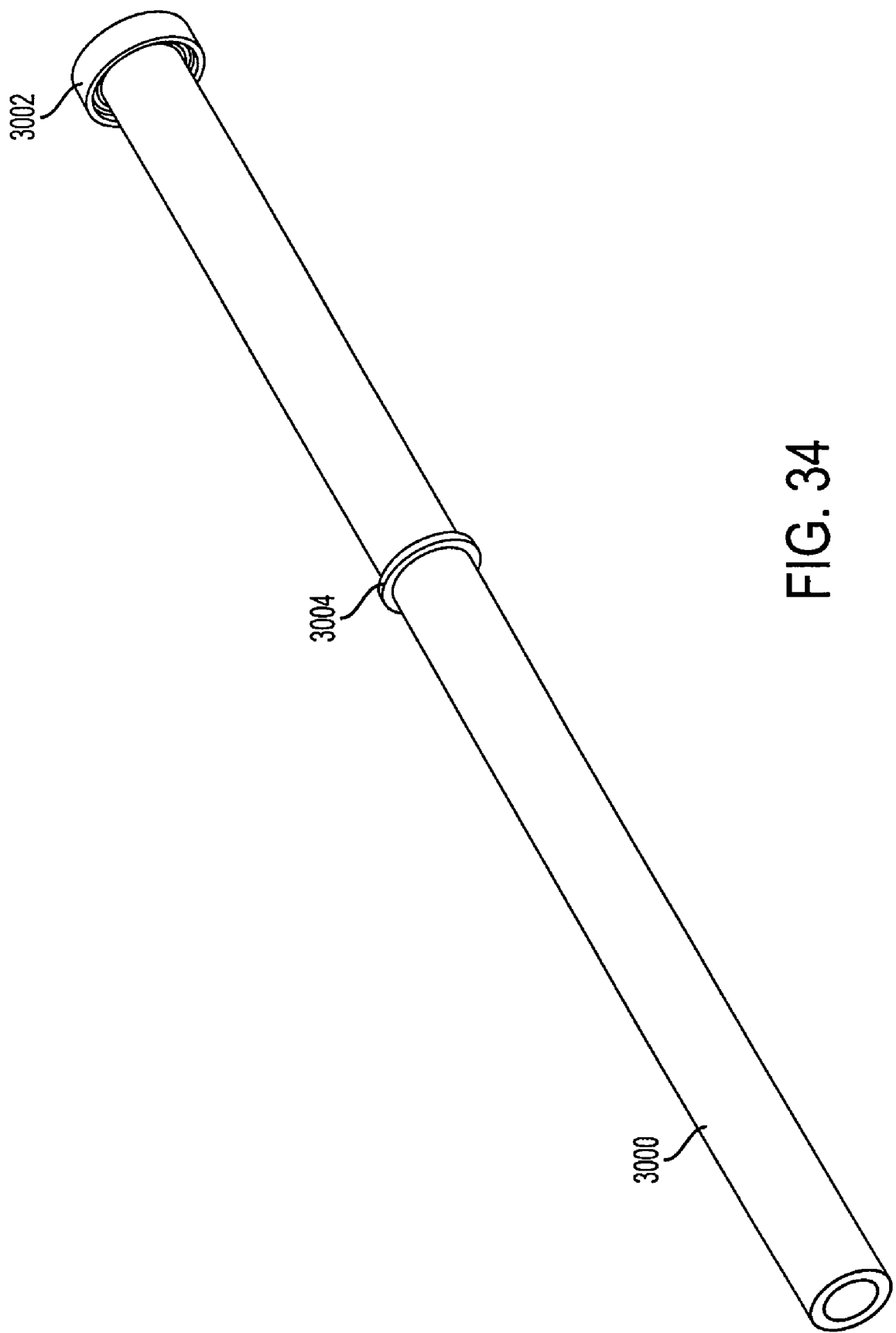
FIG. 34 is a view of an outer rod according to an embodiment of the invention.

FIG. 34 is a view of an outer rod according to an embodiment of the invention. The outer rod 3000 includes a stopping mechanism 3004 and a locking mechanism 3002. In an embodiment, the outer rod 3000 can include only a stopping mechanism 3004 or only a locking mechanism 3002. In another embodiment, the outer rod 3000 can include multiple stopping mechanisms and multiple locking mechanisms. In yet another embodiment, the outer rod 3000 includes no locking mechanisms and no stopping mechanisms.

While the principles of the disclosure have been illustrated in relation to the exemplary embodiments shown herein, the principles of the disclosure are not limited thereto and include any modification, variation or permutation thereof.

What is claimed is:

1. An intragastric space-occupying device configured to be positioned within a stomach for treating excessive weight or obesity in mammals, comprising:
   a first cylindrical cage configured to be positioned along a lesser curvature of the stomach, the first cylindrical cage having closed ends and a first rail extending longitudinally along the first cylindrical cage;
   a second cylindrical cage slidably connected to the first cylindrical cage, the second cylindrical cage having open ends, a hollow channel between the open ends, a first track extending longitudinally along the second cylindrical cage and slidably connected to the first rail, and a second track extending longitudinally along the second cylindrical cage;
   and a third cylindrical cage slidably connected to the second cylindrical cage, and configured to be positioned along a greater curvature of the stomach, the third cylindrical cage having closed ends and a second rail extending longitudinally along the third cylindrical cage and slidably connected to the second track;
   the first cylindrical cage is shorter in length than the second cylindrical cage, the third cylindrical cage is longer in length than the first cylindrical cage, and the third cylindrical cage is shorter in length than the second cylindrical cage.

2. The intragastric space-occupying device of claim 1, wherein each cage has a curved cylindrical shape.

3. The intragastric space-occupying device of claim 1, wherein each cage is made of a material selected from one of a nickel titanium or a stainless steel.

4. The intragastric space-occupying device of claim 1, wherein each cage has an external coating made from an elastomeric material.

5. The intragastric space-occupying device of claim 1, wherein the second cylindrical cage has an internal coating made from an elastomeric material.

* * * * *